US012398391B2

(12) United States Patent
Wang et al.

(10) Patent No.: US 12,398,391 B2
(45) Date of Patent: Aug. 26, 2025

(54) SEMI-RANDOM BARCODES FOR NUCLEIC ACID ANALYSIS

(71) Applicant: QIAGEN SCIENCES, LLC, Germantown, MD (US)

(72) Inventors: Yexun Wang, Ellicott City, MD (US); Zhong Wu, Poolesville, MD (US)

(73) Assignee: QIAGEN Sciences, LLC, Germantown, MD (US)

( * ) Notice: Subject to any disclaimer, the term of this patent is extended or adjusted under 35 U.S.C. 154(b) by 645 days.

(21) Appl. No.: 14/796,279

(22) Filed: Jul. 10, 2015

(65) Prior Publication Data

US 2016/0017320 A1 Jan. 21, 2016

Related U.S. Application Data

(60) Provisional application No. 62/024,590, filed on Jul. 15, 2014.

(51) Int. Cl.
*C12N 15/10* (2006.01)
*C12Q 1/6806* (2018.01)
*C12Q 1/6809* (2018.01)
*C12Q 1/6869* (2018.01)

(52) U.S. Cl.
CPC ....... *C12N 15/1093* (2013.01); *C12Q 1/6806* (2013.01); *C12Q 1/6809* (2013.01); *C12Q 1/6869* (2013.01)

(58) Field of Classification Search
CPC .......... C12N 15/1093; C12Q 1/6806; C12Q 1/6809; C12Q 1/6869; C12Q 2563/179; C12Q 2525/179
See application file for complete search history.

(56) References Cited

U.S. PATENT DOCUMENTS 5,846,719 A * 12/1998 Brenner ............. C12N 15/1065
506/3
2010/0323348 A1 12/2010 Hamady et al.
2013/0116130 A1 5/2013 Fu et al.
2014/0024541 A1 1/2014 Richards et al.
2014/0065609 A1 3/2014 Hicks et al.

FOREIGN PATENT DOCUMENTS

| WO | 01/23401 A2 | 4/2001 | |
|---|---|---|---|
| WO | 2005/080604 A2 | 9/2005 | |
| WO | 2010/086622 A1 | 8/2010 | |
| WO | 2013/123442 A1 | 8/2013 | |
| WO | 2013/130674 A1 | 9/2013 | |
| WO | WO2013142389 * | 9/2013 | ............. C04B 20/04 |
| WO | 2014/071361 A1 | 5/2014 | |

OTHER PUBLICATIONS

Kayushin et al. (Nucleic Acids Research, 1996, vol. 24, No. 19, pp. 3748-3755).*
Brenner et al., "In vitro cloning of complex mixtures of DNA on microbeads: Physical separation of differentially expressed cDNAs," *PNAS* 97(4):1665-1670 (Feb. 15, 2000).
Casbon et al., "A method for counting PCR template molecules with application to next-generation sequencing," *Nucleic Acids Research* 39(12):e81 (8 pages) (2011).
Fu et al., "Counting individual DNA molecules by the stochastic attachment of diverse labels," *PNAS* 108(22):9026-9031 (May 31, 2011).
Jabara et al., "Accurate sampling and deep sequencing of the HIV-1 protease gene using a Primer ID," *PNAS* 108(50):20166-20171 (Dec. 13, 2011).
Kinde et al., "Detection and quantification of rare mutations with massively parallel sequencing," *PNAS* 108(23):9530-9535 (Jun. 7, 2011).
Kivioja et al., "Counting absolute numbers of molecules using unique molecular identifiers," *Nature Methods* 9(1) (5 pages) (Jan. 2012).
Kozarewa et al., "Amplification-free Illumina sequencing-library preparation facilitates improved mapping and assembly of (G+C)-biased genomes," *Nature Methods* 6(4) (5 pages) (Apr. 2009).
Liang et al., "Theoretical and experimental assessment of degenerate primer tagging in ultra-deep applications of next-generation sequencing," *Nucleic Acids Research* 42(12):e98 (10 pages) (2014).
Patwardhan et al., "Massively parallel functional dissection of mammalian enhancers in vivo," *Nature Biotechnology* 30(3) (9 pages) (Mar. 2012).
Schmitt et al., "Detection of ultra-rare mutations by next-generation sequencing," *PNAS* 109(36):14508-14513 (Sep. 4, 2012).

(Continued)

*Primary Examiner* — Sahana S Kaup
(74) *Attorney, Agent, or Firm* — Seed Intellectual Property Law Group LLP

(57) ABSTRACT

The present disclosure provides oligonucleotides that comprise semi-random barcode sequences. Such oligonucleotides may be incorporated into reverse transcription primers, PCR primers, or portions of sequencing adapters in preparing sequencing libraries. The resulting sequencing libraries can be used for accurate sequencing, including DNA or RNA counting and mutation detection. Methods and kits for preparing sequencing adapters and sequencing libraries are also provided.

22 Claims, 12 Drawing Sheets

Specification includes a Sequence Listing.

(56) References Cited

OTHER PUBLICATIONS

Shiroguchi et al., "Digital RNA sequencing minimizes sequence-dependent bias and amplification noise with optimized single-molecule barcodes," *PNAS* 109(4):1347-1352 (Jan. 24, 2012).
Zagordi et al., "Error correction of next-generation sequencing data and reliable estimation of HIV quasispecies," *Nucleic Acids Research* 38(21):7400-7409 (2010).
Kayushin et al., "A convenient approach to the synthesis of trinucleotide phosphoramidites—synthons for the generation of oligonucleotide/peptide libraries," *Nucleic Acids Research* 24(19):3748-3755, 1996.
Knappik et al., "Fully Synthetic Human Combinatorial Antibody Libraries (HuCAL) Based on Modular Consensus Frameworks and CDRs Randomized with Trinucleotides," *J. Mol. Biol.* 296:57-86, 2000.

\* cited by examiner

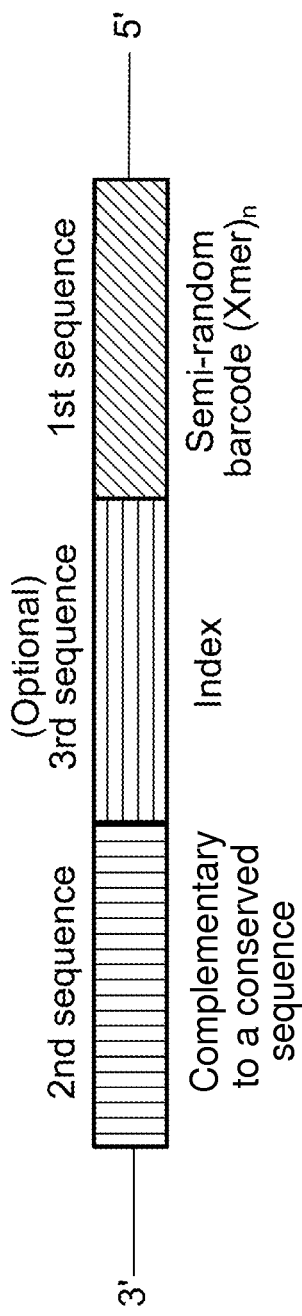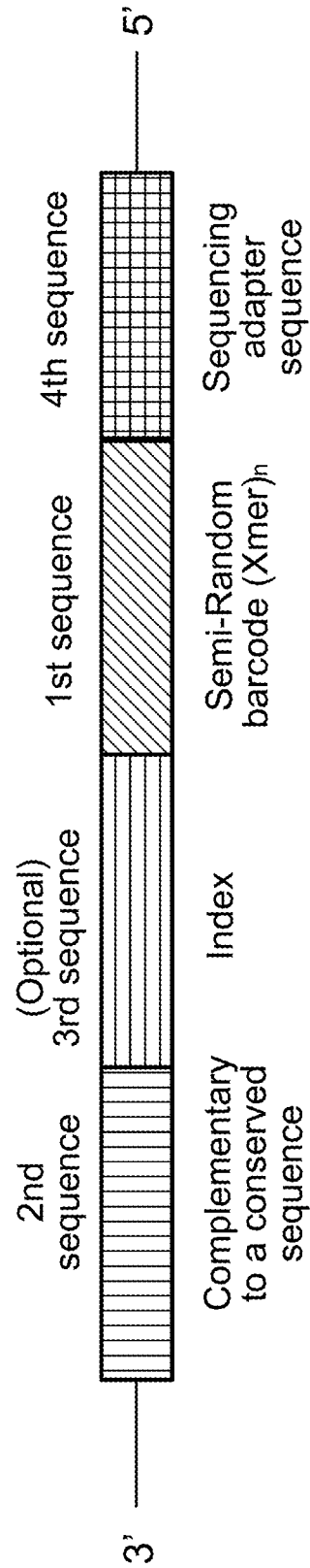

SEQUENCE LISTING

```
<160> NUMBER OF SEQ ID NOS: 24

<210> SEQ ID NO 1
<211> LENGTH: 59
<212> TYPE: DNA
<213> ORGANISM: Artificial Sequence
<220> FEATURE:
<223> OTHER INFORMATION: exemplary sequencing adapter
<220> FEATURE:
<221> NAME/KEY: misc_feature
<222> LOCATION: (1)...(59)
<223> OTHER INFORMATION: n = A,T,C or G

<400> SEQUENCE: 1
acactctttc cctacacgac gctcttccga tctnnnnnnn nnnnnnnnnn nnnncagtt      59

<210> SEQ ID NO 2
<211> LENGTH: 58
<212> TYPE: DNA
<213> ORGANISM: Artificial Sequence
<220> FEATURE:
<223> OTHER INFORMATION: Exemplary sequencing adapter
<220> FEATURE:
<221> NAME/KEY: misc_feature
<222> LOCATION: (1)...(58)
<223> OTHER INFORMATION: n = A,T,C or G

<400> SEQUENCE: 2
actgnnnnnn nnnnnnnnnn nnnnnagatc ggaagagcgg ttcagcagga atgccgag       58

<210> SEQ ID NO 3
<211> LENGTH: 19
<212> TYPE: DNA
<213> ORGANISM: Artificial Sequence
<220> FEATURE:
<223> OTHER INFORMATION: Exemplary sequencing adapter

<400> SEQUENCE: 3
gttcagcagg aatgccgag                                                  19

<210> SEQ ID NO 4
<211> LENGTH: 14
<212> TYPE: DNA
<213> ORGANISM: Artificial Sequence
<220> FEATURE:
<223> OTHER INFORMATION: Exemplary sequencing adapter

<400> SEQUENCE: 4
agatcggaag agcg                                                       14

<210> SEQ ID NO 5
<211> LENGTH: 19
<212> TYPE: DNA
<213> ORGANISM: Artificial Sequence
<220> FEATURE:
<223> OTHER INFORMATION: Exemplary sequencing adapter

<400> SEQUENCE: 5
acactctttc cctacacga                                                  19

<210> SEQ ID NO 6
<211> LENGTH: 14
<212> TYPE: DNA
<213> ORGANISM: Artificial Sequence
<220> FEATURE:
<223> OTHER INFORMATION: Exemplary sequencing adapter

<400> SEQUENCE: 6
```

-continued cgctcttccg atct                                                                14

<210> SEQ ID NO 7
<211> LENGTH: 55
<212> TYPE: DNA
<213> ORGANISM: Artificial Sequence
<220> FEATURE:
<223> OTHER INFORMATION: Exemplary A adapter sequence
<220> FEATURE:
<221> NAME/KEY: misc_feature
<222> LOCATION: (1)...(55)
<223> OTHER INFORMATION: n = A,T,C or G

<400> SEQUENCE: 7
ccatctcatc cctgcgtgtc tccgactcag nnnnnnnnnn nnnnnnnnnn nagcg            55

<210> SEQ ID NO 8
<211> LENGTH: 59
<212> TYPE: DNA
<213> ORGANISM: Artificial Sequence
<220> FEATURE:
<223> OTHER INFORMATION: Exemplary A adapter sequence
<220> FEATURE:
<221> NAME/KEY: misc_feature
<222> LOCATION: (1)...(59)
<223> OTHER INFORMATION: n = A,T,C or G

<400> SEQUENCE: 8
cgctnnnnnn nnnnnnnnnn nnnnnctgag tcggagacac gcagggatga gatggagtt       59

<210> SEQ ID NO 9
<211> LENGTH: 30
<212> TYPE: DNA
<213> ORGANISM: Artificial Sequence
<220> FEATURE:
<223> OTHER INFORMATION: Exemplary A adapter sequence

<400> SEQUENCE: 9
ctgagtcgga gacacgcagg gatgagatgg                                       30

<210> SEQ ID NO 10
<211> LENGTH: 30
<212> TYPE: DNA
<213> ORGANISM: Artificial Sequence
<220> FEATURE:
<223> OTHER INFORMATION: Exemplary A adapter sequence

<400> SEQUENCE: 10
ccatctcatc cctgcgtgtc tccgactcag                                       30

<210> SEQ ID NO 11
<211> LENGTH: 41
<212> TYPE: DNA
<213> ORGANISM: Artificial Sequence
<220> FEATURE:
<223> OTHER INFORMATION: Ion Torrent single end P1 adapter sequence

<400> SEQUENCE: 11
ccactacgcc tccgctttcc tctctatggg cagtcggtga t                          41

<210> SEQ ID NO 12
<211> LENGTH: 43
<212> TYPE: DNA
<213> ORGANISM: Artificial Sequence
<220> FEATURE:
<223> OTHER INFORMATION: Ion Torrent single end P1 adapter sequence

<400> SEQUENCE: 12
atcaccgact gcccatagag aggaaagcgg aggcgtagtg gtt         43

<210> SEQ ID NO 13
<211> LENGTH: 48
<212> TYPE: DNA
<213> ORGANISM: Artificial Sequence
<220> FEATURE:
<223> OTHER INFORMATION: Paired-end P1 adapter sequence

<400> SEQUENCE: 13
ccactacgcc tccgctttcc tctctatggg cagtcggtga tcctcagc    48

<210> SEQ ID NO 14
<211> LENGTH: 50
<212> TYPE: DNA
<213> ORGANISM: Artificial Sequence
<220> FEATURE:
<223> OTHER INFORMATION: Paired-end P1 adapter sequence

<400> SEQUENCE: 14
gctgaggatc accgactgcc catagagagg aaagcggagg cgtagtggtt  50

<210> SEQ ID NO 15
<211> LENGTH: 48
<212> TYPE: DNA
<213> ORGANISM: Artificial Sequence
<220> FEATURE:
<223> OTHER INFORMATION: Paired-end P1 adapter sequence

<400> SEQUENCE: 15
gctgaggatc accgactgcc catagagagg aaagcggagg cgtagtgg    48

<210> SEQ ID NO 16
<211> LENGTH: 48
<212> TYPE: DNA
<213> ORGANISM: Artificial Sequence
<220> FEATURE:
<223> OTHER INFORMATION: Paired-end P1 adapter sequence

<400> SEQUENCE: 16
ccactacgcc tccgctttcc tctctatggg cagtcggtga tcctcagc    48

<210> SEQ ID NO 17
<211> LENGTH: 30
<212> TYPE: DNA
<213> ORGANISM: Artificial Sequence
<220> FEATURE:
<223> OTHER INFORMATION: Paired-end A adapter sequence

<400> SEQUENCE: 17
ccatctcatc cctgcgtgtc tccgactcag                       30

<210> SEQ ID NO 18
<211> LENGTH: 32
<212> TYPE: DNA
<213> ORGANISM: Artificial Sequence
<220> FEATURE:
<223> OTHER INFORMATION: Paired-end A adapter sequence

<400> SEQUENCE: 18
ctgagtcgga gacacgcagg gatgagatgg tt                    32

<210> SEQ ID NO 19
<211> LENGTH: 30

```
<212> TYPE: DNA
<213> ORGANISM: Artificial Sequence
<220> FEATURE:
<223> OTHER INFORMATION: Paired-end A adapter sequence

<400> SEQUENCE: 19
ctgagtcgga gacacgcagg gatgagatgg                                            30

<210> SEQ ID NO 20
<211> LENGTH: 30
<212> TYPE: DNA
<213> ORGANISM: Artificial Sequence
<220> FEATURE:
<223> OTHER INFORMATION: Paired-end A adapter sequence

<400> SEQUENCE: 20
ccatctcatc cctgcgtgtc tccgactcag                                            30

<210> SEQ ID NO 21
<211> LENGTH: 37
<212> TYPE: DNA
<213> ORGANISM: Artificial Sequence
<220> FEATURE:
<223> OTHER INFORMATION: Barcoded Illumina Strand (Semi-Random) sequence
<220> FEATURE:
<221> NAME/KEY: modified_base
<222> LOCATION: 1
<223> OTHER INFORMATION: 5' phospate group
<220> FEATURE:
<221> NAME/KEY: misc_feature
<222> LOCATION: (1)...(37)
<223> OTHER INFORMATION: n = A, T, C or G

<400> SEQUENCE: 21
gatcnnnnnn nnnnnnagat cggaagagca cacgtct                                    37

<210> SEQ ID NO 22
<211> LENGTH: 58
<212> TYPE: DNA
<213> ORGANISM: Artificial Sequence
<220> FEATURE:
<223> OTHER INFORMATION: Illumina Fill-In Primer

<400> SEQUENCE: 22
aatgatacgg cgaccaccga gatctacact ctttccctac acgacgctct tccgatct             58

<210> SEQ ID NO 23
<211> LENGTH: 31
<212> TYPE: DNA
<213> ORGANISM: Artificial Sequence
<220> FEATURE:
<223> OTHER INFORMATION: Sequencing primer

<400> SEQUENCE: 23
acactctttc cctacacgac gctcttccga t                                          31

<210> SEQ ID NO 24
<211> LENGTH: 32
<212> TYPE: DNA
<213> ORGANISM: Artificial Sequence
<220> FEATURE:
<223> OTHER INFORMATION: Sequencing primer

<400> SEQUENCE: 24
gtgactcgag ttcagacgtg tgctcttccg at                                         32
```

SEMI-RANDOM BARCODES FOR NUCLEIC ACID ANALYSIS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 830109_407_SEQUENCE_LISTING.txt. The text file is 5.3 KB, was created on Sep. 16, 2015, and is being submitted electronically via EFS-Web.

BACKGROUND

1. Technical Field

The present disclosure relates to oligonucleotides, kits, and methods for nucleic acid analysis, especially nucleic acid sequencing.

2. Description of the Related Art

Next generation sequencing (NGS) technology has been used in DNA sequencing for mutation detection as well as in RNA sequencing for transcriptome profiling. However, the error rate associated with this technology in current sequencing platforms prevents it from confident identification of rare mutations. Similarly, the accurate counting of transcripts in RNA sequencing is complicated by sequencing-dependent bias and amplification noise from library amplification, clonal amplification and sequencing.

Previous studies have assigned each template molecule with a unique barcode to correct amplification bias and sequencing errors, and the unique barcode can be either a random sequence of oligonucleotide or a sequence predefined oligonucleotide. However, a random sequence barcode can be frequently misidentified due to sequencing errors in the barcode region, and the cost for generating large varieties of sequence predefined barcodes is very high.

BRIEF DESCRIPTION OF THE DRAWINGS

FIG. 5A is a schematic representation of an exemplary PCR primer that comprises a semi-random barcode sequence.

FIG. 5B is a schematic representation of another exemplary PCR primer that comprises a semi-random barcode sequence.

DETAILED DESCRIPTION

Figure 1:
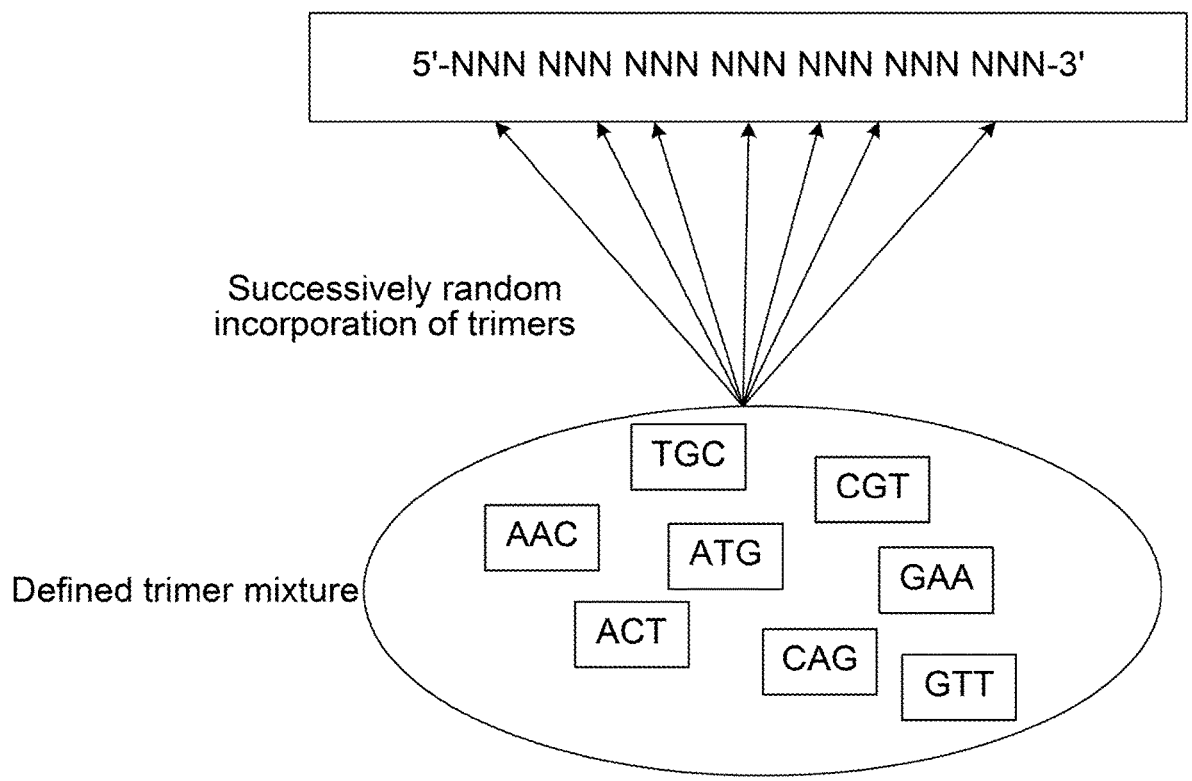
FIG. 1 is schematic representation of an exemplary semi-random barcode sequence and its synthesis.

In the following description, any ranges provided herein include all the values in the ranges. It should also be noted that the term "or" is generally employed in its sense including "and/or" (i.e., to mean either one, both, or any combination thereof of the alternatives) unless the content dictates otherwise. Also, as used in this specification and the appended claims, the singular forms "a," "an," and "the" include plural referents unless the content dictates otherwise. The terms "include," "have," "comprise" and their variants are used synonymously and to be construed as non-limiting.

SUMMARY OF PRESENT DISCLOSURE AND ADVANTAGES

NGS (also referred to as "massively parallel sequencing") is useful in mutation detection and transcriptome profiling. However, a number of errors can be introduced during sample preparation and sequencing process. These error prone processes include sequence-dependent bias and amplification noise from reverse transcription, adapter ligation, library amplification by PCR, solid-phase clonal amplification and sequencing as well as polymerase errors generating point mutations during amplification and sequencing.

The present disclosure provides methods for reducing errors in sequencing and thus improving accuracy in mutation detection and transcriptome profiling. Such methods use semi-random barcodes to tag sequencing fragments before amplification to reduce bias and sequencing errors. Because amplicons derived from a particular starting molecule can be identified based on semi-random barcodes, variations in the sequence or copy number of identically tagged sequencing reads can be considered as technical errors and subsequently corrected.

Using semi-random barcodes as disclosed herein is advantageous over other methods of exogenous tagging of sequencing fragments. For example, unlike random barcodes, semi-random barcodes allow corrections to errors in the barcodes arising from library preparation, amplification and sequencing. In addition, semi-random barcodes are also advantageous over barcodes with defined sequences. Although errors in barcodes with defined sequences may be identified, it is difficult and expensive to generate a large number of such barcodes, which limits their use in NGS.

Oligonucleotides Comprising Semi-Random Barcode Sequences

In one aspect, the present application provides oligonucleotides that comprise semi-random barcode sequences, including sequencing adapters, reverse transcription primers and PCR primers.

1. Semi-Random Barcode Sequences

The term "semi-random barcode sequences," "semi-random sequences," or "semi-random barcodes" refers to a population of semi-random nucleotide sequences each consisting of (Xmer)n, wherein Xmer is 3-mer (i.e., a 3-nucleotide oligonucleotide, also referred to as "trimer"), 4-mer (i.e., a 4-nucleotide oligonucleotide, also refers to as "tetramer")), 5-mer (i.e., a 5-nucleotide oligonucleotide, also refers to as "pentamer"), or 6-mer (i.e., a 6-nucleotide oligonucleotide, also refers to as "hexamer"), and n is an integer from 2 to 10. Each nucleotide sequence in the population is referred to as "semi-random barcode sequence," "semi-random barcode," or "semi-random sequence."

In certain embodiments, the semi-random sequence consist of (Xmer)n, wherein Xmer is 3-mer, and n is 2, 3, 4, 5, 6, 7, 8, 9, or 10, preferably 4, 5, 6, 7, 8 or 9.

In certain embodiments, Xmer is 4-mer, and n is 2, 3, 4, 5, 6, 7, 8, or 9, preferably 2, 3, 4, 5, 6, or 7.

In certain embodiments, Xmer is 5-mer, and n is 2, 3, 4, 5, 6, 7, or 8, preferably 2, 3, 4, 5, or 6.

In certain embodiments, Xmer is 6-mer, and n is 2, 3, 4, 5, 6, or 7 preferably 2, 3, 4, or 5.

The semi-random barcode sequences may be synthesized from a mixture of Xmers with defined sequences. For example, in certain embodiments, the semi-random barcodes consist of (Xmer)n, wherein Xmer is 3-mer and n is 7. In other words, the semi-random barcodes are a population of 21 bp oligonucleotides that consist of 7 trimers. Such semi-random barcodes may be synthesized with 7 successive steps during each of which steps, a random trimer from a defined trimer mixture may be incorporated.

In the above example, the trimer may be selected from commonly available trimers corresponding to amino acid coding sequences. For instance, from the pool of 20 trimers used for amino acid codons, 8 of them can be selected for the defined mixture of trimers used for semi-random barcode synthesis. The sequences of these 8 trimers may be: AAC, ACT, ATG, CAG, CGT, GAA, GTT, and TGC. For a 21 bp oligonucleotide barcode, each three nucleotides may be added randomly from the 8 trimer mixture. Thus, the possible sequence varieties of the 21 bp barcode is $8^7$ (i.e., 2,097,152). The synthesis of a 21 bp oligonucleotide barcode with a defined trimer mixture consisting of the above-noted 8 trimers is shown in FIG. 1.

The trimers from which that semi-random barcodes may be synthesized are not limited to amino acid codons. They may include those that do not code any amino acids (e.g., stop codons).

A defined Xmer mixture for synthesizing semi-random barcodes may have 2, 3, 4, 5, 6, 7, 8, 9, 10, 11, 12, 13, 14, 15, 16, 17, 18, 19, 20, 21, 22, 23, 24, or 25, or at least 2, 3, 4, 5, 6, 7, 8, 9, 10, 11, 12, 13, 14, 15, 16, 17, 18, 19, 20, 21, 22, 23, 24, or 25, different Xmers.

The number of different semi-random barcode sequences synthesized from a defined Xmer mixture may be at least 100, 200, 300, 400, 500, 1,000, 2,000, 3,000, 4,000, 5,000, 10,000, 50,000, 100,000, 50,000, 100,000, 500,000, or 1,000,000.

Preferably, each Xmer (e.g., trimer, tetramer, pentamer, and hexamer) has at least 2 bases different from another Xmer in a defined Xmer mixture so that any single-base variant within each Xmer block in sequencing reads can be identified as errors, not a different barcode.

In certain embodiments, each Xmer (e.g., tetramer, pentamer, and hexamer) has at least 3 bases different from another Xmer in a defined Xmer mixture so that any single- or 2-base variant within each Xmer block in sequencing reads can be identified as errors, not a different barcode.

In certain embodiments, each Xmer (e.g., pentamer and hexamer) has at least 4 bases different from another Xmer in a defined Xmer mixture so that any 1-, 2-, or 3-base variant within each Xmer block in sequencing reads can be identified as errors, not a different barcode.

2. Double-Stranded (ds) Sequencing Adapters

In one aspect, the present disclosure provides oligonucleotides that comprise semi-random barcode sequences and are useful in preparing ds sequencing adapters for sequencing ds nucleic acids.

a. Single-Stranded (ss) Oligonucleotide Sequences (with Semi-Random Barcodes)

The semi-random barcode sequences may be incorporated into ds sequencing adapters. Thus, in one aspect, the present disclosure provides a plurality of ss oligonucleotides (also referred to as "a population of ss oligonucleotides"), wherein each oligonucleotide comprises from the 5' to 3' direction, a $1^{st}$ sequence and a $2^{nd}$ sequence; the $1^{st}$ sequence is a semi-random sequence consisting of (Xmer)n as provided herein, and the $2^{nd}$ sequence (i) is at least 10 nucleotides in length, (ii) is fully or substantially complementary to a target sequence, and (iii) is the same among the plurality of oligonucleotides. Each of such oligonucleotides may anneal to another oligonucleotide to prepare sequencing adapters as described in detail below.

An "oligonucleotide" refers to a short polymer composed of deoxyribonucleotides, ribonucleotides or combinations thereof. Oligonucleotides are generally between 10 and 150 nucleotides, such as between 10 and 30 nucleotides, between 30 and 60 nucleotides, between 60 and 90 nucleotides, between 90 and 120 nucleotides, and between 120 and 150 nucleotides in length. Preferably, oligonucleotides are between 30 and 100 nucleotides, and more preferably between 40 and 80 nucleotides in length.

(1) $1^{st}$ Sequence

Figure 2:
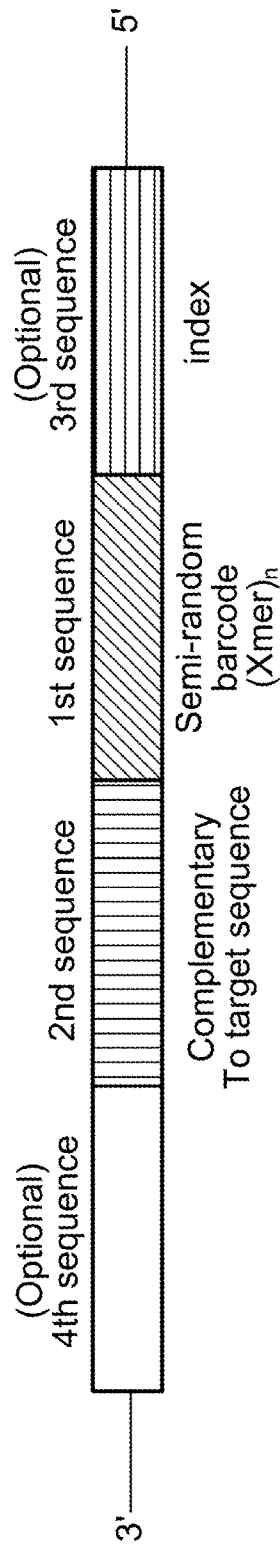
FIG. 2 is a schematic representation of an exemplary single-stranded oligonucleotide that comprises a semi-random barcode sequence.

A schematic representation of an exemplary ss oligonucleotide useful in preparing a ds sequencing adapter is shown in FIG. 2. Any of the semi-random barcode sequences as described herein may be incorporated in the plurality of oligonucleotides as the $1^{st}$ sequence.

(2) $2^{nd}$ Sequence

The $2^{nd}$ sequence is located 3' to the $1^{st}$ sequence. A sequence ("Sequence X") is located 3' to another sequence ("Sequence Y") if the 5' terminus of Sequence X is located 3' to the 3' terminus of Sequence Y. The 5' terminus of Sequence X may be, or may not be, immediately next to the 3' terminus of Sequence Y.

Conversely, a sequence ("Sequence X") is located 5' to another sequence ("Sequence Y") if the 3' terminus of Sequence X is located 5' to the 5' terminus of Sequence Y. The 3' terminus of Sequence X may be, or may not be, immediately next to the 5' terminus of Sequence Y.

The $2^{nd}$ sequence should be sufficiently long to anneal to a target sequence of interest to allow extension of the target sequence using the oligonucleotide as the template under appropriate conditions for preparing a sequencing adapter. For example, the $2^{nd}$ sequence may be at least 10, 11, 12, 13, 14, or 15 nucleotides in length.

The $2^{nd}$ sequence is fully or substantially complementary to a target sequence of interest. The terms "complementary" and "complement" and their variants, as used herein, refer to any two nucleic acid sequences that form a hybridized duplex by base pairing. One nucleic acid sequence may be completely or fully complimentary to another nucleic acid sequence if all of the nucleotides in the one nucleic acid sequence form base pairing with nucleotides in the corresponding antiparallel positions on the other nucleic acid nucleotides. "Partial" complementarity describes nucleic acid sequences in which at least 50%, but less than 100%, of the residues of one nucleic acid fragment are complementary to residues in the other nucleic acid fragment. A primer is "substantially complementary" to a target nucleic acid if at least 85% (e.g., at least 90%, 95% or 98%) of the residues of the primer are complementary to residues in the target nucleic acid.

In addition, the $2^{nd}$ sequence is the same among a given population of oligonucleotides. This allows the preparation of a population of sequencing adapters using (1) the given population of oligonucleotides and (2) a single oligonucleotide that comprises the target sequence to which the $2^{nd}$ sequence is fully or substantially complementary.

(3) $3^{rd}$ Sequence

The oligonucleotide provided herein may further comprise a $3^{rd}$ sequence that (i) has a defined sequence that is 3 to 8 nucleotides in length, (ii) is located 5' to the $2^{nd}$ sequence, and (iii) is the same among the oligonucleotides of a given population of oligonucleotides.

The defined sequence of the $3^{rd}$ sequence is preferably located immediately next to the semi-random barcode sequence, and more preferably located immediately 5' to the semi-random barcode sequence (i.e., the 5' terminus of the semi-random barcode sequence is located immediately 3' to the 3' terminus of the $3^{rd}$ sequence (see, FIG. 2). Such an arrangement allows an easy distinction between a sample DNA sequence and the semi-random barcode sequence after sequencing experiment based on the defined sequence of the $3^{rd}$ sequence. More specifically, as described in detail below, the 5' terminus of the $3^{rd}$ sequence may be linked to a sample DNA sequence in generating a sequencing library. Thus, the $3^{rd}$ sequence is located between the sample DNA and the semi-random barcode sequence, and provides the delineation between these two sequences.

In addition, the $3^{rd}$ sequence may also serve as an index for multiplex experiment in which different indices are used to tag different samples. More detailed description is provided below in connection with preparing multiple sets of plurality of oligonucleotides.

The $3^{rd}$ sequence should be sufficiently long so that it may be used to distinguish a sample DNA sequence and a semi-random barcode sequence in sequencing reads. However, it should not be too long so that it takes up too much sequencing capacity. In certain embodiments, the $3^{rd}$ sequence is 3, 4, 5, 6, 7, or 8 nucleotides in length.

Similar to the $2^{nd}$ sequence, the $3^{rd}$ sequence is the same among a given population of oligonucleotides.

(4) $4^{th}$ Sequence

The oligonucleotide may further comprise a $4^{th}$ sequence that is (i) located 3' to the $2^{nd}$ sequence, and (ii) is the same among the oligonucleotides in a given population.

The $4^{th}$ sequence may provide a sequence for designing an amplification primer for amplifying a sequencing library and a sequencing primer for generating sequencing data.

The $4^{th}$ sequence preferably has one or more phosphorothioate bonds at or near its 3' terminus so that a DNA polymerase with a 3' 5' exonuclease activity will not be able to cleave nucleotides at or near the 3' terminus of the target sequence.

Preferably, the $4^{th}$ sequence comprises a portion of the sequences of adapters typically used in or suitable for sequencing with known sequencing instruments, such as ILLUMINA® instruments. For example, the $4^{th}$ sequence may comprise one strand (or a portion thereof that is at least 10 nucleotides in length) of the floppy overhang of an adapter used with ILLUMINA® instruments ("Illumina adapter"). The "floppy overhang" of an adapter refers to a terminal portion of an adapter where the two strands of the adapter do not anneal to each other.

Similar to the $2^{nd}$ sequence and the $3^{rd}$ sequence (if present), the $4^{th}$ sequence is the same among a given population of oligonucleotides.

(5) 5' phosphorylation

Preferably, the oligonucleotides provided herein are phosphorylated at their 5' termini. The 5' phosphate groups allow sequencing adapters generated from the oligonucleotides to be ligated with sample DNA molecules.

b. Sets of ss Oligonucleotide Sequences (with Semi-Random Barcodes and Index Sequences)

In a related aspect, the present disclosure provides a plurality of sets of ss oligonucleotides, wherein each set comprises the plurality of ss oligonucleotides that comprise, in addition to the $1^{st}$ and $2^{nd}$ sequences, a $3^{rd}$ sequence as described above, and wherein the oligonucleotides in different sets are identical to each other except in the $3^{rd}$ sequences thereof. In each set of oligonucleotides, the $1^{st}$ sequence is a semi-random sequence consisting of (Xmer)n as described above.

As described above, the $3^{rd}$ sequence has a defined sequence and may be used as an index to tag different samples. While different oligonucleotides in each set have an identical $3^{rd}$ sequence, oligonucleotides in different sets have different $3^{rd}$ sequences. Thus, sequencing adapters generated from oligonucleotides in one set ("Set A") may be used to generate a sequencing library for DNA fragments of one sample ("Sample A"), and sequencing adapters generated from oligonucleotides in another set ("Set B") may be used to generate a sequencing library for DNA fragments of another sample ("Sample B"). The sequencing reads for Sample A will have the $3^{rd}$ sequence unique to set A, and those for Sample B will have the $3^{rd}$ sequence unique to set B. Thus, the plurality of sets of oligonucleotides provided herein increases the degree of multiplicity of massively parallel sequencing.

c. Methods for Preparing ds Sequencing Adapters

In a further related aspect, the present disclosure provides a method for preparing a plurality of ds sequencing adapters. The method comprises: (1) annealing a plurality of ss oligonucleotides ("$1^{st}$ oligonucleotides") or a plurality of sets of ss oligonucleotides ("sets of $1^{st}$ oligonucleotides") described herein to a $2^{nd}$ ss oligonucleotide that comprises the target sequence ("Sequence B"), and (2) extending the 3' terminus of the $2^{nd}$ oligonucleotide using the $1^{st}$ oligonucleotides as templates.

The $2^{nd}$ sequence of the $1^{st}$ oligonucleotides or the sets of $1^{st}$ oligonucleotides is fully or substantially complementary to the target sequence of the $2^{nd}$ oligonucleotide so that they may anneal to each other under appropriate conditions where the 3' terminus of the target sequence may be further extended using the oligonucleotides as templates.

The term "adapter" refers to (a) an at least partially double-stranded oligonucleotide that can be ligated to a double-stranded DNA molecule or fragment of interest, or (b) a single stranded oligonucleotide that can be ligated to a single-stranded nucleic acid molecule. The at least partially double-stranded oligonucleotide is referred to as "double-stranded adapter" or "ds adapter," while the single-stranded oligonucleotide is referred to as "single-stranded adapter" or "ss adapter."

The ds adapter and the ds DNA molecule or fragment may contain overhangs that complement to each other to facilitate ligation between the adapter and the DNA molecule or fragment.

The term "sequencing adapter" refers to (a) an at least partially double-stranded adapter that can be ligated to one or more double-stranded DNA molecules or fragments of interest so that the ds DNA molecules or fragments may be subsequently sequenced, or (b) a single-stranded adapter that can be ligated to one or more single-stranded nucleic acid molecules or fragments of interest. The at least partially ds adapter is referred to as "double-stranded sequencing adapter" or "ds sequencing adapter," while the single-stranded oligonucleotide is referred to as "single-stranded sequencing adapter" or "ss sequencing adapter."

The double-stranded DNA may be completely double stranded or may have a short 3'-overhang at one or both strands (e.g., 1-, 2-, or 3-nucleotide overhangs). The short 3'-overhang facilitate ligation between the ds DNA and a ds sequencing adapter having a complementary overhang.

A ds sequencing adapter is generally 15-150 bps in length in its double-stranded region, such as 15-30, 30-45, 45-60, 60-90, 90-120, or 120-150 bps, preferably 20-100 bps, and more preferably 30-80 bps.

The target sequence of the $2^{nd}$ oligonucleotide has the same length as the $2^{nd}$ sequence of the $1^{st}$ oligonucleotide, and thus has at least 10, 11, 12, 13, 14, or 15 nucleotides.

The target sequence of the $2^{nd}$ oligonucleotide may be any sequence that is fully or substantially complementary to the $2^{nd}$ sequence of the $1^{st}$ oligonucleotide. Preferably, the target sequence of the $2^{nd}$ oligonucleotide comprises a portion that is at least 10 nucleotides long of one strand of a fully or partially double-stranded sequencing adapter, preferably a sequencing adapter typically used in or suitable for sequencing with known sequencing instruments, such as ILLUMINA® instruments and Life Technology ION TORRENT® instruments.

The $2^{nd}$ oligonucleotide may further comprise another sequence ("Sequence D") located 5' to the target sequence. Sequence D may be fully or substantially complementary to the $4^{th}$ sequence of the $1^{st}$ oligonucleotides. Alternatively, Sequence D is not substantially complementary to the $4^{th}$ sequence of the $1^{st}$ oligonucleotide. Thus, when a $1^{st}$ oligonucleotide anneals to the $2^{nd}$ oligonucleotide via the $2^{nd}$ sequence of the $1^{st}$ oligonucleotide and the target sequence of the $2^{nd}$ oligonucleotide, the $4^{th}$ sequence of the $1^{st}$ oligonucleotide and Sequence D of the $2^{nd}$ oligonucleotide forms floppy overhangs as those in adapters typically used with ILLUMINA® instruments. In such a case, Sequence D of the $2^{nd}$ oligonucleotide, in addition to the $4^{th}$ sequence of the $1^{st}$ oligonucleotide, may be used in designing amplification primers for amplifying sequencing libraries and sequencing primers. In certain embodiments, sequence D of the $2^{nd}$ oligonucleotide may comprise one strand (or a portion thereof that is at least 10 nucleotides in length) of the floppy overhang of an Illumina adapter.

Methods for annealing a $1^{st}$ oligonucleotide to a $2^{nd}$ oligonucleotide are known in the art. The two oligonucleotides may be mixed together in an appropriate buffer, preferably the buffer is also suitable for performing primer extension, and incubated at a high temperature (e.g., 95° C.) for a period of time (e.g., 10 minutes). The temperature of the mixture may then be reduced gradually (e.g., 5° C. decrease per 5 minutes) to allow the annealing of the two oligonucleotides. An exemplary method is described in Example 1.

After annealing between the $1^{st}$ and $2^{nd}$ oligonucleotides, the 3' terminus of the $2^{nd}$ oligonucleotide may be extended using the $1^{st}$ oligonucleotides as templates in a reaction mixture that comprises a DNA polymerase (e.g., the Klenow fragment). An exemplary method is also described in Example 1.

The at least partially double-stranded oligonucleotides resulting from the extension of the $2^{nd}$ oligonucleotide may be directly used to ligate to blunt end double-stranded sample DNA molecules or fragments to generate sequencing libraries. Alternatively, a single- or multiple-nucleotide overhang (e.g., a T-overhang) may be added to the at least partially double-stranded oligonucleotides in the presence of a DNA polymerase (e.g., exo⁻ Klenow fragment). An exemplary method for adding a T-overhang is described in Example 1.

d. Kits for Preparing Double-Stranded Sequencing Adapters

In another related aspect, the present disclosure provides a kit for preparing ds sequencing adapters. The kit comprises (i) a plurality of ss oligonucleotides ("$1^{st}$ oligonucleotides") or a plurality of sets of ss oligonucleotides ("sets of $1^{st}$ oligonucleotides) described herein, and (ii) a $2^{nd}$ ss oligonucleotide that comprises the target sequence ("Sequence B").

The plurality of $1^{st}$ oligonucleotides, the plurality of sets of oligonucleotides, and the $2^{nd}$ oligonucleotide are as described elsewhere in the present disclosure, especially in connection with the methods for preparing sequencing adapters.

The kit may further comprise one or more of the following additional components: a DNA polymerase (e.g., Klenow fragment), a buffer appropriate for oligonucleotide extension, dNTPs, and dTTP.

e. Double-Stranded Sequencing Adapters

In a related aspect, the present disclosure provides a plurality of ds sequencing adapters, wherein each sequencing adapter comprises a $1^{st}$ oligonucleotide as described herein and a $2^{nd}$ oligonucleotide as described herein, and wherein the $1^{st}$ oligonucleotide anneals to the $2^{nd}$ oligonucleotide.

More specifically, the present disclosure provides a plurality of ds sequencing adapters, wherein each sequencing adapter comprises: (a) an oligonucleotide ("$1^{st}$ oligonucleotide" or "$1^{st}$ strand") of the plurality of oligonucleotides provided herein, the $1^{st}$ oligonucleotide comprises from the 5' to 3' direction: (i) a $1^{st}$ sequence that is semi-random sequence consisting of (Xmer)n, wherein Xmer is 3-mer, 4-mer, 5-mer, or 6-mer, and n is an integer from 2 to 8, and (ii) a $2^{nd}$ sequence that is at least 10 nucleotides in length, is fully or substantially complementary to a target sequence, and is the same among the plurality of oligonucleotides, and (b) a $2^{nd}$ oligonucleotide (also referred to as "$2^{nd}$ strand" or "filled-in strand") that comprises from the 3' to 5' direction: (i) a sequence ("Sequence A") that is fully complementary to the $1^{st}$ sequence of the $1^{st}$ oligonucleotide of the sequence adapter, and (ii) the target sequence ("Sequence B") to which the $2^{nd}$ sequence of the $1^{st}$ oligonucleotide is complementary, wherein the $1^{st}$ oligonucleotide anneals to the $2^{nd}$ oligonucleotide.

In certain embodiments, the $1^{st}$ oligonucleotide further comprises a $3^{rd}$ sequence that (i) has a defined sequence that is 3 to 8 nucleotides in length, (ii) is located 5' to the $2^{nd}$ sequence, preferably 5' to the $1^{st}$ sequence, and (iii) is the same among the plurality of the $1^{st}$ oligonucleotides, and the $2^{nd}$ oligonucleotide further comprises a sequence ("Sequence C") that is located 3' to Sequence B, preferably 3' to Sequence A, and is fully complementary to the $3^{rd}$ sequence of the $1^{st}$ oligonucleotide.

In certain embodiments, the $1^{st}$ oligonucleotide further comprises a $4^{th}$ 4 sequence that (i) is located 3' to the $2^{nd}$ sequence, and (ii) is the same among the plurality of the $1^{st}$ oligonucleotides. In such embodiments, the $1^{st}$ oligonucleotide may or may not comprise a $3^{rd}$ sequence as described above, and the $2^{nd}$ oligonucleotide may or may not comprise Sequence C as described above.

In certain embodiments, the $2^{nd}$ oligonucleotide further comprises a sequence ("Sequence D") located 5' to Sequence B. In such embodiments, the $1^{st}$ oligonucleotide may or may not comprise a $4^{th}$ sequence. In the embodiments where the $1^{st}$ oligonucleotide comprises a $4^{th}$ sequence, Sequence D of the $2^{nd}$ oligonucleotide may or may not be fully or substantially complementary to the $4^{th}$ sequence of the $1^{st}$ oligonucleotides, and may or may not have the same length as the $4^{th}$ sequence of the $1^{st}$ oligonucleotides.

Figure 3:
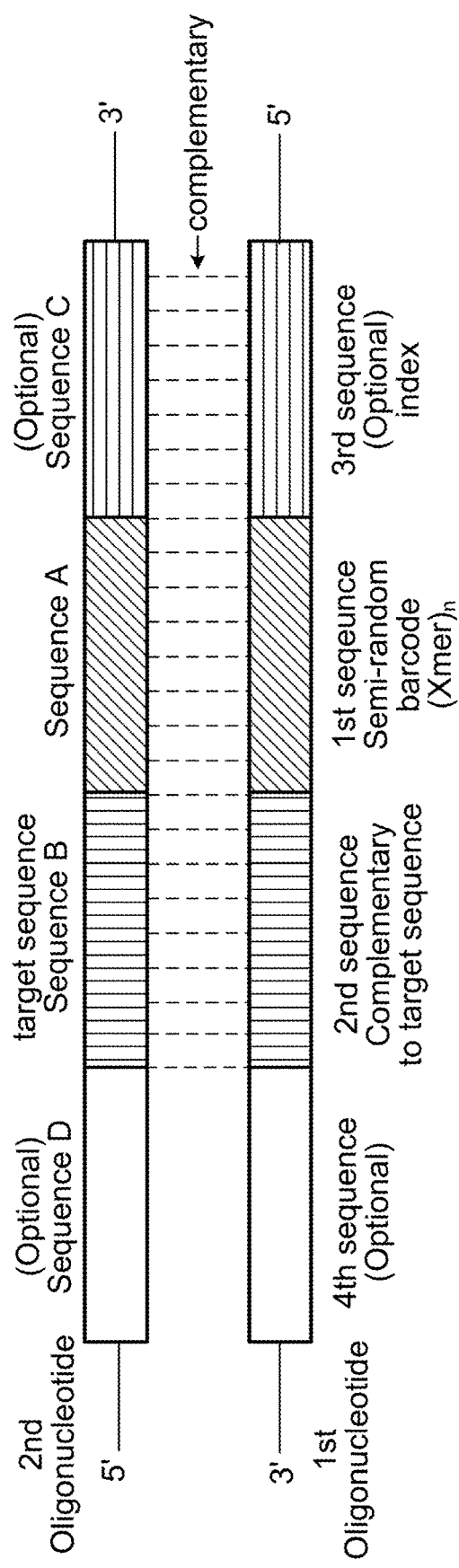
FIG. 3 is a schematic representation of an exemplary double-stranded adapter that comprises a semi-random barcode sequence.

A schematic representation of an exemplary sequencing adapter that comprises $1^{st}$, $2^{nd}$, $3^{rd}$, and $4^{th}$ sequences in the $1^{st}$ oligonucleotide and Sequence A, Sequence B, Sequence C, and Sequence D in the $2^{nd}$ oligonucleotide is shown in FIG. 3.

Each of the plurality of sequencing adapters may have a single- or multiple-nucleotide 3'-overhang in the $2^{nd}$ oligonucleotide to facilitate ligation with sample DNA molecules or fragments containing a complementary 3'-overhang.

The plurality of sequencing adapters may be made according to the methods for making sequencing adapters provided herein.

An exemplary sequencing adapter suitable for sequencing with ILLUMINA® instruments is shown below:

```
                                              (SEQ ID NO: 1)
5' ACA CTC TTT CCC TAC ACG ACG CTC TTC CGA TCT (nnn)7 CAGTT 3'

(SEQ ID NO: 2)
3' GAG CCG TAA GGA CGA CTT GGC GAG AAG GCT AGA (NNN)7 GTCA 5'
```

In the above exemplary Illumina adapter, the lower strand is the $1^{st}$ oligonucleotide or strand, and the upper strand is the $2^{nd}$ oligonucleotide (i.e., the $2^{nd}$ strand or the filled-in strand). In the $1^{st}$ oligonucleotide, the underlined region

```
                                              (SEQ ID NO: 3)
(GAG CCG TAA GGA CGA CTT G)
``` is the $4^{th}$ sequence, the bold region (GC GAG AAG GCT AGA) (SEQ ID NO: 4) is the $2^{nd}$ sequence, the (NNN)$_7$ region is the $1^{st}$ sequence (i.e., the semi-random barcode sequence), and the italicized region (GTCA) is the $3^{rd}$ sequence (i.e., the index sequence). In the $2^{nd}$ oligonucleotide, the underlined region

```
                                              (SEQ ID NO: 5)
(ACA CTC TTT CCC TAC ACG A)
``` is Sequence D, the bold region (CG CTC TTC CGA TCT) (SEQ ID NO: 6) is the target sequence (i.e., Sequence B), the (nnn)$_7$ region is Sequence A, and the italicized region (CAGT) is Sequence C. While Sequence B, Sequence A, and Sequence C of the $2^{nd}$ oligonucleotide are fully complementary to the $2^{nd}$ sequence, the $1^{st}$ sequence, and the $3^{rd}$ sequence of the $1^{st}$ oligonucleotide, respectively, Sequence D of the $2^{nd}$ oligonucleotide is not substantially complementary to the $4^{th}$ sequence of the $1^{st}$ oligonucleotide. The "T" at the 3' terminus of the $2^{nd}$ oligonucleotide is a single-nucleotide overhang that facilitates ligation with sample DNA molecules or fragments having a 3'-"A" overhang.

For generating single-end read using ION TORRENT® instruments, an exemplary A adapter is shown below.

Ion Torrent Single End A Adapter:

```
                                              (SEQ ID NO: 7)
5' CCATCTCATCCCTGCGTGTCTCCGACTCAG (nnn)7 AGCG 3'

(SEQ ID NO: 8)
3' T*T*G*A*GGTAGAGTAGGGACGCACAGAGGCTGAGTC (NNN)7

TCGC 5'
```

* represents a phosphorothioate bond.

In the above exemplary adapter for generating Ion Torrent single end reads, the lower strand is the $1^{st}$ oligonucleotide or strand, and the upper strand is the $2^{nd}$ oligonucleotide (i.e., the $2^{nd}$ strand or the filled-in strand). In the $1^{st}$ oligonucleotide, the underlined region (T*T*G*A*) is the $4^{th}$ sequence, the bold region (GGTAGAGTAGGGACGCACAGAGGCTGAGTC) (SEQ ID NO: 9) is the $2^{nd}$ sequence, the (NNN)$_7$ region is the $1^{st}$ sequence (i.e., the semi-random barcode sequence), and the italicized region (TCGC) is the $3^{rd}$ sequence (i.e., the index sequence). In the $2^{nd}$ oligonucleotide, there is no underlined region that would correspond to Sequence D, the bold region (CCATCTCATCCCTGCGTGTCTCCGACTCAG) (SEQ ID NO: 10) is the target sequence (i.e., Sequence B), the (nnn)$_7$ region is Sequence A, and the italicized region (AGCG) is Sequence C. Sequence B, Sequence A, and Sequence C of the $2^{nd}$ oligonucleotide are fully complementary to the $2^{nd}$ sequence, the $1^{st}$ sequence, and the $3^{rd}$ sequence of the $1^{st}$ oligonucleotide, respectively.

There is no change to P1 adapter (as shown below) typically used for generating Ion Torrent single end reads in this case. In other words, the P1 adapter does not need to incorporate a semi-random barcode sequence to generate single end reads when using ION TORRENT® instruments.

Ion Torrent Single End P1 Adapter:

```
                                              (SEQ ID NO: 11)
5' CCACTACGCCTCCGCTTTCCTCTCTATGGGCAGTCGGTGAT 3'

(SEQ ID NO: 12)
3' T*T*GGTGATGCGGAGGCGAAAGGAGAGATACCCGTCAGCCACTA
5'
```

* represents a phosphorothioate bond.

For generating paired-end read using ION TORRENT® instruments, semi-random barcode sequences are added to the end of both A adapter and P1 adapters. An exemplary paired-end P1 adapter is shown below:
Paired-End P1 Adapter:

```
                                              (SEQ ID NO: 13)
5'- CCACTACGCCTCCGCTTTCCTCTCTATGGGCAGTCGGTGATCCT

CAGC-Barcode^-Index^-3'

(SEQ ID NO: 14)
3'-T*T*GGTGATGCGGAGGCGAAAGGAGAGATACCCGTCAGCCACTA

GGAGTCG-Barcode-Index-5'
```

* represents a phosphorothioate bond.

In the above exemplary P1 adapter for generating Ion Torrent paired-end reads, the lower strand is the $1^{st}$ oligonucleotide or strand, and the upper strand is the $2^{nd}$ oligonucleotide (i.e., the $2^{nd}$ strand or the filled-in strand). In the $1^{st}$ oligonucleotide, the underlined region (T*T*) is the $4^{th}$ sequence, the bold region (GGTGATGCG-GAGGCGAAAGGAGAGATACCCGTCAGCCACTAG-GAGTCG) (SEQ ID NO: 15) is the $2^{nd}$ sequence, the "Barcode" region is the $1^{st}$ sequence (i.e., the semi-random barcode sequence), and the "Index" region (consisting of, for example, 3-5 nucleotides) is the $3^{rd}$ sequence. In the $2^{nd}$ oligonucleotide, there is no underlined region that would be Sequence D, the bold region (CCAC-TACGCCTCCGCTTTCCTCTCTATGGGCAGTCGGT-GATCCTCAGC) (SEQ ID NO: 16) is the target sequence (i.e., Sequence B), the "Barcode'" region is Sequence A, and the "Index'" is Sequence C. Sequence B, Sequence A, and Sequence C of the $2^{nd}$ oligonucleotide are fully complementary to the $2^{nd}$ sequence, the $1^{st}$ sequence, and the $3^{rd}$ sequence of the $1^{st}$ oligonucleotide, respectively.
Paired-End A Adapter:

```
                                              (SEQ ID NO: 17)
5'- CCATCTCATCCCTGCGTGTCTCCGACTCAG-Barcode'-

Index'-3'

(SEQ ID NO: 18)
3'-T*T*GGTAGAGTAGGGACGCACAGAGGCTGAGTC-Barcode-

Index-5'
```

* represents a phosphorothioate bond.

In the above exemplary A adapter for generating Ion Torrent paired-end reads, the lower strand is the $1^{st}$ oligonucleotide or strand, and the upper strand is the $2^{nd}$ oligonucleotide (i.e., the $2^{nd}$ strand or the filled-in strand). In the $1^{st}$ oligonucleotide, the underlined region (T*T*) is to the $4^{th}$ sequence, the bold region (GGTAGAGTAGGGACGCACAGAGGCTGAGTC) (SEQ ID NO: 19) is the $2^{nd}$ sequence, the "Barcode" region is the $1^{st}$ sequence (i.e., the semi-random barcode sequence), and the "Index" region (consisting of, for example, 3-5 nucleotides) is the $3^{rd}$ sequence. In the $2^{nd}$ oligonucleotide, there is no underlined region that would be Sequence D, the bold region (CCATCTCATCCCTGCGTGTCTCCGACTCAG) (SEQ ID NO: 20) is the target sequence (i.e., Sequence B), the "Barcode'" region is Sequence A, and the "Index'" is Sequence C. Sequence B, Sequence A, and Sequence C of the $2^{nd}$ oligonucleotide are fully complementary to the $2^{nd}$ sequence, the $1^{st}$ sequence, and the $3^{rd}$ sequence of the $1^{st}$ oligonucleotide, respectively.

f. Sets of Double-Stranded Sequencing Adapters

In a related aspect, the present disclosure provides a plurality of sets of ds sequencing adapters wherein each set comprises a plurality of ds sequencing adapters. Each sequencing adapter in each set comprises a $1^{st}$ oligonucleotide and a $2^{nd}$ oligonucleotide, wherein the $1^{st}$ oligonucleotide anneals to the $2^{nd}$ oligonucleotide. The $1^{st}$ oligonucleotide comprises: (i) a $1^{st}$ sequence that is semi-random sequence consisting of (Xmer)n, wherein Xmer is 3-mer, 4-mer, 5-mer, or 6-mer, and n is an integer from 2 to 8, and (ii) a $2^{nd}$ sequence that is at least 10 nucleotides in length, is located 3' to the $1^{st}$ sequence, is fully or substantially complementary to a target sequence, and is the same among the oligonucleotides in the same set, and (iii) a $3^{rd}$ sequence that has a defined sequence that is 3 to 8 nucleotides in length, is located 5' to the $2^{nd}$ sequence, preferably 5' to the $1^{st}$ sequence, and is the same among the $1^{st}$ oligonucleotides in that set. The $2^{nd}$ oligonucleotide comprises: (i) a sequence ("Sequence A") that is fully complementary to the $1^{st}$ sequence of the $1^{st}$ oligonucleotide of the sequence adapter, (ii) the target sequence ("Sequence B") located 5' to Sequence A, and (iii) a sequence ("Sequence C") that is located 3' to Sequence B, preferably 3' to Sequence A, and is fully complementary to the $3^{rd}$ sequence of the $1^{st}$ oligonucleotides in that set. Thus, sequence adapters in each set are identical to each other except different adapters have different $1^{st}$ sequences (i.e., semi-random barcodes) in $1^{st}$ oligonucleotides and different corresponding (complementary) Sequence A in the $2^{nd}$ oligonucleotides. In the plurality of set of sequencing adapters provided herein, sequence adapters in different sets are identical to each other except in the $3^{rd}$ sequence of the $1^{st}$ oligonucleotides and in corresponding (complementary) Sequence C of the $2^{nd}$ oligonucleotides. The different $3^{rd}$ sequence of the $1^{st}$ oligonucleotides in different sets of sequencing adapters allow different sets of sequencing adapters to be ligated to and thus tag DNA molecules or fragments from different samples.

In certain embodiments, in each set, the $1^{st}$ oligonucleotide further comprises a $4^{th}$ sequence that (i) is located 3' to the $2^{nd}$ sequence, and (ii) is the same among the plurality of the $1^{st}$ oligonucleotides in the same set.

In certain embodiments, in each set, the $2^{nd}$ oligonucleotide further comprises a sequence ("Sequence D") located 5' to Sequence B. In such embodiments, the $1^{st}$ oligonucleotide may or may not comprise a $4^{th}$ sequence. In the embodiments where the $1^{st}$ oligonucleotide comprises a $4^{th}$ sequence, Sequence D of the $2^{nd}$ oligonucleotide may or may not be fully or substantially complementary to the $4^{th}$ sequence of the $1^{st}$ oligonucleotides.

Each sequencing adapter of the plurality of sets may have a single- or multiple-nucleotide 3'-overhang in the $2^{nd}$ oligonucleotide to facilitate ligation with sample DNA molecules or fragments containing a complementary 3'-overhang.

The sequencing adapters of each set may be made according to the methods for making sequencing adapters described above. Multiple sets of such sequencing adapters may be combined to provide a plurality of sets of sequencing adapters as described herein.

3. Reverse Transcription Primers

The present disclosure also provides a plurality of reverse transcription primers (also referred to as "a population of reverse transcription primers") that may be used to incorporate semi-random barcode sequences into sequencing libraries via reverse transcription. Each primer comprises from the 5' to 3' direction, a $1^{st}$ sequence and a $2^{nd}$ sequence; the $1^{st}$ sequence is a semi-random sequence consisting of (Xmer)n, and the $2^{nd}$ sequence comprises a sequence that is complementary to a target RNA sequence.

Reverse transcription is a process of generating cDNA from an RNA template in the presence of a reverse transcriptase. A "reverse transcription primer" is an oligonucleotide that is complementary to a portion of an RNA molecule and leads to addition of nucleotides to the 3' end of the primer in the presence of a reverse transcriptase using the RNA molecule as a template. A reverse transcription primer may be 15-100 nucleotides in length, such as 15-30, 30-45, 45-60, 60-80, or 80-100 nucleotides in length, preferably 20-50 nucleotides in length.

The description of semi-random sequence consisting of (Xmer)n provided above and the description of the $1^{st}$ sequence in connection with single-stranded oligonucleotide sequences for generating ds sequencing adapters are applicable to the semi-random sequence and the $1^{st}$ sequence in reverse transcription primers disclosed herein and thus referred to in this section. The $2^{nd}$ sequence may be a sequence that is complementary to a conserved sequence of a RNA molecule of interest. A "conserved" sequence, as used herein, refers to a sequence in a RNA molecule of interest that is at least 10 nucleotides in length (e.g., at least 12, 14, 16, 18, or 20 nucleotides in length) and has at least 70% sequence identity (e.g., at least 80%, 85%, 90% or 95%) over the length of the sequence among the same RNA molecules from two or more different species.

Preferably, the $2^{nd}$ sequence comprises a poly(T) sequence (e.g., a sequence comprising 6-20 thymidines, preferably 10-18 thymidines) that is complementary to 3'-poly(A) tails of mRNAs.

In certain embodiments, the reverse transcription primer may further comprise a $3^{rd}$ sequence that (i) has a defined sequence that is 3 to 8 nucleotides in length, (ii) is located 5' to the $2^{nd}$ sequence, and (iii) is the same among the reverse transcription primers of a given population.

Figure 4A:
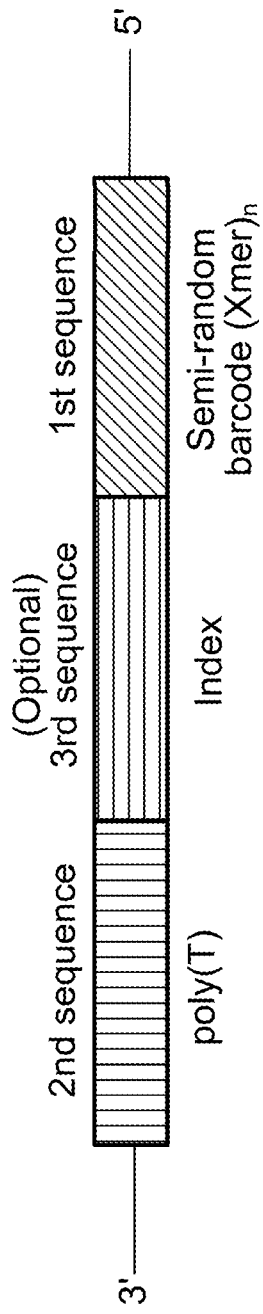
FIG. 4A is a schematic representation of an exemplary reverse transcription primer that comprises a semi-random barcode sequence.

The defined sequence of the $3^{rd}$ sequence is preferably located immediately next to the semi-random barcode sequence. In certain embodiments, the defined sequence of the $3^{rd}$ sequence is located immediately 3' to the semi-random barcode sequence (i.e., the 5' terminus of the $3^{rd}$ sequence is immediately next to the 3' terminus of the semi-random barcode sequence). A schematic representation of such a reverse transcription primer is shown in FIG. 4A. Alternatively, the defined sequence of the $3^{rd}$ sequence is located immediately 5' to the semi-random barcode sequence (i.e., the 3' terminus of the $3^{rd}$ sequence is immediately next to the 5' terminus of the semi-random barcode sequence).

The $3^{rd}$ sequence may serve as an index for multiplex experiment in which different indices are used to tag different samples. Thus, in a related aspect, the present disclosure provides a plurality of sets of reverse transcription primers wherein each set comprises a plurality of reverse transcription primers. Each reverse transcription primer in each set comprises, in addition to a $1^{st}$ sequence and a $2^{nd}$ sequence, a $3^{rd}$ sequence as described above. While different reverse transcription primers in each set have an identical $3^{rd}$ sequence, reverse transcription primers in different sets have different $3^{rd}$ sequences, but are otherwise identical to each other.

In certain preferred embodiments, the reverse transcription primer may further comprise a $4^{th}$ sequence that (i) is located 5' to the $1^{st}$ sequence, the $2^{nd}$ sequence, and the $3^{rd}$ sequence (if present), and (ii) is the same among the reverse transcription primers of a given population.

Figure 4B:
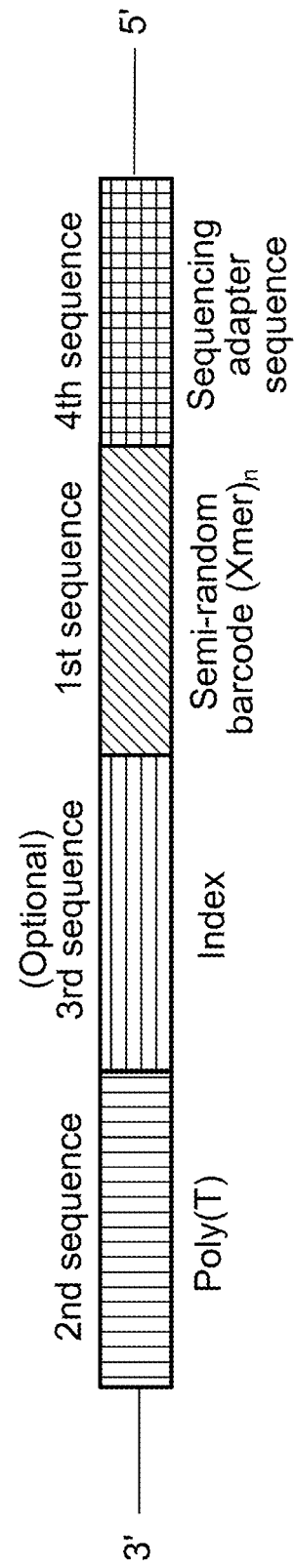
FIG. 4B is a schematic representation of another exemplary reverse transcription primer that comprises a semi-random barcode sequence.

Preferably, the $4^{th}$ sequence comprises a sequencing adapter sequence. A schematic representation of such a preferred reverse transcription primer is shown in FIG. 4B.

A "sequencing adapter sequence" refers to a sequence of one strand of ds sequencing adapter or a sequence of a ss sequencing adapter. It typically comprises a sequence for designing an amplification primer for amplifying a sequencing library and a sequencing primer for generating sequencing data. Preferably, the sequencing adapter sequence comprises a portion of an adapter typically used in or suitable for sequencing with known sequencing instruments, such as ILLUMINA® and Life Technologies' Ion Torrent instruments.

4. PCR Primers

The present disclosure also provides a plurality of PCR primers (also referred to as "a population of PCR primers") that may be used to incorporate semi-random barcode sequences into sequencing libraries via primer extension. Each primer comprises from the 5' to 3' direction, a $1^{st}$ sequence and a $2^{nd}$ sequence; the $1^{st}$ sequence is a semi-random sequence consisting of (Xmer)n, and the $2^{nd}$ sequence comprises a sequence that is at least substantially complementary to a conserved sequence of a region of interest.

Polymerase chain reaction (PCR) is a well-known technique for amplifying a DNA molecule to generate multiple copies of the DNA molecule (see, U.S. Pat. Nos. 4,683,195 and 4,683,202). It relies on thermal cycling consisting of cycles of repeated heating and cooling of the reaction for DNA melting and enzymatic replication of the DNA. PCR uses primers containing sequences complementary to a target region along with a DNA polymerase. As PCR progresses, the DNA generated is itself used as a template for replication, setting in motion a chain reaction in which the DNA template is exponentially amplified.

A "PCR primer" is an oligonucleotide that is complementary to a sample DNA molecule or fragment and leads to addition of nucleotides to the 3' terminus of the primer in the presence of a DNA polymerase during PCR using the sample DNA molecule or fragment as a template. A PCR primer may be 15-100 nucleotides in length, such as 15-30, 30-45, 45-60, 60-80, or 80-100 nucleotides in length, preferably 20-50 nucleotides in length.

The description of semi-random sequence consisting of (Xmer)n provided above and the description of the $1^{st}$ sequence in connection with single-stranded oligonucleotide sequences for generating ds sequencing adapters are applicable to the semi-random sequence and the $1^{st}$ sequence in PCR primers disclosed herein and thus referred to in this section.

A region (e.g., a gene) of interest may be any region (e.g., any gene) with one or more conserved sequences, such as house-keeping genes. Exemplary genes of interest include genes encoding 3-phosphate dehydrogenase (GAPDH), tubulins, cyclophilin, albumin, actins, and rRNAs (e.g., prokaryotic 5S, 16S, and 23S rRNAs and eukaryotic 5S, 5.8S, 18S and 28S rRNAs). See, Eisenberg and Levanon, Trends in Genetics 29:569-74, 2013. In certain preferred embodiments, the region of interest is a bacterial 16S rRNA gene.

A "conserved" sequence of a region (e.g., a gene) of interest, as used herein, refers to a sequence in a region (e.g., a gene) of interest that is at least 10 nucleotides in length and has at least 70% sequence identity (e.g., at least 80%, 85%, 90% or 95%) among the same genes from two or more different species.

In certain embodiments, the PCR primer may further comprise a $3^{rd}$ sequence that (i) has a defined sequence that is 3 to 8 nucleotides in length, (ii) is located 5' to the $2^{nd}$ sequence, and (iii) is the same among the PCR primers of a given population.

The defined sequence of the $3^{rd}$ sequence is preferably located immediately next to the semi-random barcode sequence. In certain embodiments, the defined sequence of the $3^{rd}$ sequence is located immediately 3' to the semi-random barcode sequence (i.e., the 5' terminus of the $3^{rd}$ sequence is immediately next to the 3' terminus of the semi-random barcode sequence). A schematic representation of such a PCR primer is shown in FIG. 5A. Alternatively, the defined sequence of the $3^{rd}$ sequence is located immediately 5' to the semi-random barcode sequence (i.e., the 3' terminus of the $3^{rd}$ sequence is immediately next to the 5' terminus of the semi-random barcode sequence).

The $3^{rd}$ sequence may serve as an index for multiplex experiment in which different indices are used to tag different samples. Thus, in a related aspect, the present disclosure provides a plurality of sets of PCR primers wherein each set comprises a plurality of PCR primers. Each PCR primer in each set comprises, in addition to a $1^{st}$ sequence and a $2^{nd}$ sequence, a $3^{rd}$ sequence as described above. While different PCR primers in each set have an identical $3^{rd}$ sequence, PCR primers in different sets have different $3^{rd}$ sequences, but are otherwise identical to each other.

In certain preferred embodiments, the PCR primer may further comprise a $4^{th}$ sequence that (i) is located 5' to the $1^{st}$ sequence, the $2^{nd}$ sequence, and the $3^{rd}$ sequence (if present), and (ii) is the same among the PCR primers of a given population.

Preferably, the $4^{th}$ sequence comprises a sequencing adapter sequence. The term "sequencing adapter sequence" is described above. A schematic representation of such a preferred PCR primer is shown in FIG. 5B.

5. Single-Stranded Oligonucleotides for Sequencing Single-Stranded Nucleic Acids The present disclosure also provides a plurality of ss oligonucleotides (also referred to as "a population of ss oligonucleotides") that may be used to incorporate semi-random barcode sequences into sequencing libraries and useful for sequencing ss nucleic acids.

a. $1^{st}$ Arrangement

In certain embodiments, each ss oligonucleotide comprises (a) a $1^{st}$ sequence that is a semi-random sequence consisting of (Xmer)n, (b) optionally a $2^{nd}$ sequence that (i) has a defined sequence that is 3 to 8 nucleotides in length, and (ii) is the same among the oligonucleotides, and (c) a $3^{rd}$ sequence that (i) has a defined sequence, (ii) is the same among the oligonucleotides, and (iii) is located 5' to the $1^{st}$ sequence and the $2^{nd}$ sequence (if present).

The description of semi-random sequence consisting of (Xmer)n provided above and the description of the $1^{st}$ sequence in connection with ss oligonucleotide sequences for generating ds sequencing adapters are applicable to the semi-random sequence and the $1^{st}$ sequence in ss oligonucleotides disclosed herein and thus referred to in this section.

Figure 6A:
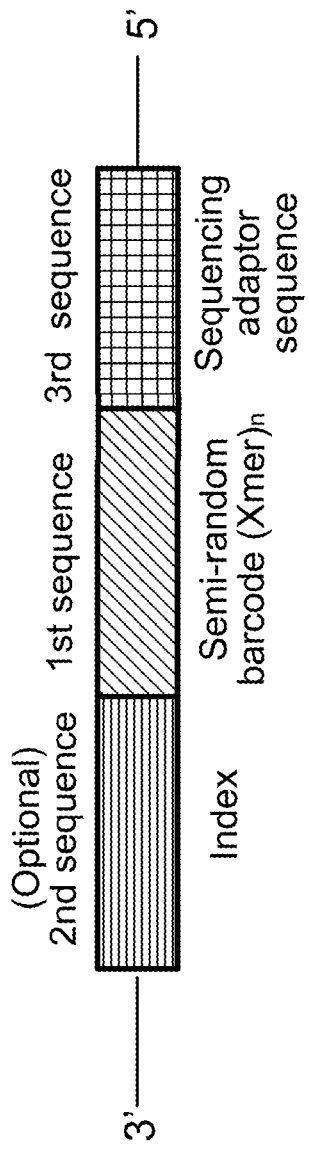
FIG. 6A is a schematic representation of an exemplary single-stranded sequencing adapter.

In certain embodiments, the ss oligonucleotide comprises the $2^{nd}$ sequence. The $2^{nd}$ sequence is preferably located immediately next to the semi-random barcode sequence. It may be located immediately 3' to the semi-random barcode sequence (i.e., the 5' terminus of the $2^{nd}$ sequence is immediately next to the 3' terminus of the semi-random barcode sequence). A schematic representation of such an oligonucleotide is shown in FIG. 6A. Alternatively, the $2^{nd}$ sequence is located immediately 5' to the semi-random barcode sequence (i.e., the 3' terminus of the $2^{nd}$ sequence is immediately next to the 5' terminus of the semi-random barcode sequence).

The $2^{nd}$ sequence may serve as an index for multiplex experiment in which different indices are used to tag different samples. Thus, in a related aspect, the present disclosure provides a plurality of sets of ss oligonucleotides wherein each set comprises a plurality of ss oligonucleotides. Each ss oligonucleotide in each set comprises, in addition to a $1^{st}$ sequence and a $3^{rd}$ sequence, a $2^{nd}$ sequence as described above. While different ss oligonucleotides in each set have an identical $2^{nd}$ sequence, ss oligonucleotides in different sets have different $2^{nd}$ sequenced, but are otherwise identical to each other.

The $3^{rd}$ sequence is located 5' to the $1^{st}$ sequence and the $2^{nd}$ sequence (if present). It is the same among the ss oligonucleotides in one or multiple sets. In certain embodiments, the $3^{rd}$ sequence compirses a sequencing adapter sequence.

b. $2^{nd}$ Arrangement

In certain embodiments, each ss oligonucleotide comprises (a) a $1^{st}$ sequence that is a semi-random sequence consisting of (Xmer)n, (b) optionally a $2^{nd}$ sequence that (i) has a defined sequence that is 3 to 8 nucleotides in length, and (ii) is the same among the oligonucleotides, and (c) a $3^{rd}$ sequence that (i) has a defined sequence, (ii) is the same among the oligonucleotides, and (iii) is located 3' to the $1^{st}$ sequence and the $2^{nd}$ sequence (if present).

The description of semi-random sequence consisting of (Xmer)n provided above and the description of the $1^{st}$ sequence in connection with ss oligonucleotide sequences for generating ds sequencing adapters are applicable to the semi-random sequence and the $1^{st}$ sequence in ss oligonucleotides disclosed herein and thus referred to in this section.

Figure 6B:
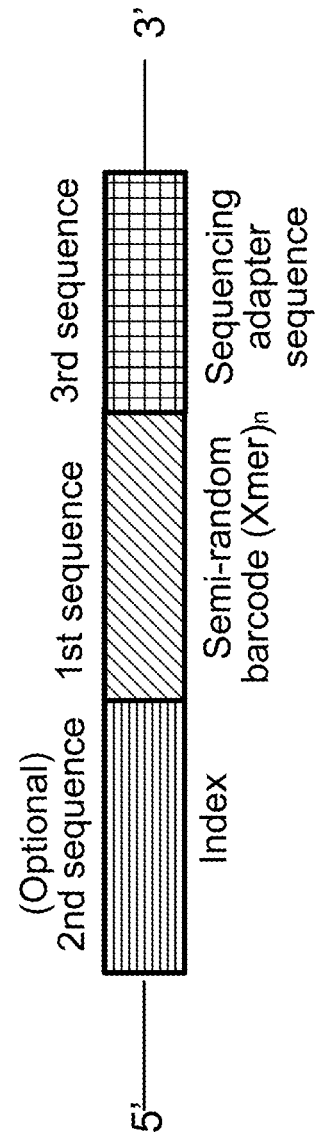
FIG. 6B is a schematic representation of another exemplary single-stranded sequencing adapter.

In certain embodiments, the ss oligonucleotide comprises the $2^{nd}$ sequence. The $2^{nd}$ sequence is preferably located immediately next to the semi-random barcode sequence. It may be located immediately 3' to the semi-random barcode sequence (i.e., the 5' terminus of the $2^{nd}$ sequence is immediately next to the 3' terminus of the semi-random barcode sequence). Alternatively, the $2^{nd}$ sequence is located immediately 5' to the semi-random barcode sequence (i.e., the 3' terminus of the $2^{nd}$ sequence is immediately next to the 5' terminus of the semi-random barcode sequence). A schematic representation of such an oligonucleotide is shown in FIG. 6B.

The $2^{nd}$ sequence may serve as an index for multiplex experiment in which different indices are used to tag different samples. Thus, in a related aspect, the present disclosure provides a plurality of sets of ss oligonucleotides wherein each set comprises a plurality of ss oligonucleotides. Each ss oligonucleotide in each set comprises, in addition to a $1^{st}$ sequence and a $3^{rd}$ sequence, a $2^{nd}$ sequence as described above. While different ss oligonucleotides in each set have an identical $2^{nd}$ sequence, ss oligonucleotides in different sets have different $2^{nd}$ sequences, but are otherwise identical to each other.

The $3^{rd}$ sequence is located 3' to the $1^{st}$ sequence and the $2^{nd}$ sequence (if present). It is the same among the ss oligonucleotides in one or multiple sets. In certain embodiments, the $3^{rd}$ sequence comprises a sequencing adapter sequence.

Methods of Using Oligonucleotides

The present disclosure also provides methods of using oligonucleotides that comprise semi-random barcode sequences, such as in preparing sequencing libraries and subsequent analysis.

1. Preparing Sequencing Libraries a. Using Double-Stranded Sequencing Adapters i. Single Set of Double-Stranded Sequencing Adapters In one aspect, the present disclosure provides a method for preparing a sequencing library that comprises (1) ligating the plurality of ds sequencing adapters that comprise a semi-random barcode sequence (i.e., the $1^{st}$ sequence of the $1^{st}$ oligonucleotide) described herein to ds DNA molecules or fragments of a sample.

The term "sequencing library" refers to a collection of ds DNA molecules or fragments of a sample that are linked to one set of ds sequencing adapters at the both ends of the DNA molecules or fragments or to two different sets of ds sequencing adapters: one set at one end of the DNA molecules or fragments, the other set at the other end of the DNA molecules or fragments. The ds sequencing adapters in each set share one or more common sequences, which allow anchoring the DNA molecules or fragments of the sequencing library to a solid surface for high throughput sequencing via sequences complementary to the common sequences of the adapter sequences immobilized to the solid surface, and may also allow the design of sequencing primers for sequencing of the DNA molecules or fragments of the sample.

The sample from which DNA molecules or fragments are sequenced may be any sample that contains nucleic acids, including materials obtained from clinical, forensic, and environmental settings. Preferably, the sample is a biological sample derived from a human, animal, plant, bacteria or fungi. The term "sample" also includes processed samples including preserved, fixed and/or stabilized samples, such as formalin fixed and paraffin-embedded (FFPE samples) and other samples that were treated with cross-linking fixatives such as glutaraldehyde.

Exemplary samples from which nucleic acids may be prepared include, but are not limited to, blood, swabs, body fluid, tissues including but not limited to, liver, spleen, kidney, lung, intestine, brain, heart, muscle, and pancreas, cell cultures, food samples, plant tissues or samples, as well as lysates, extracts, or materials and fractions obtained from the samples described above, or any cells, microorganisms and viruses that may be present on or in a sample, and the like.

Isolating target nucleic acids from a sample of interest may be performed by any method known in the art useful for nucleic acid isolation or purification. In addition, many kits for nucleic acid preparation are commercially available and may be used, including QIAamp DNA mini kit, QIAamp FFPE Tissue kit, and PAXgene DNA kit.

Genomic DNAs may be used as the starting material for preparing a sequencing library. In certain embodiments, the genomic DNAs in combination represent a whole genome. In other embodiments, the genomic DNAs in combination represent an exome (i.e., the part of a genome formed by exons). In further embodiments, the nucleic acids may be target-enriched DNA fragments generated, for example, via PCR amplification using target gene-specific primers (see, e.g., Qiagen GeneRead™ DNAseq Gene Panel Handbook).

In certain embodiments, DNA molecules (e.g., genomic DNA molecules) from a sample may be first fragmented, the resulting fragments may be then end-repaired, and optionally single or multiple nucleotides may be added to the 3' termini of the end-repaired DNA fragments to generate 3'-overhangs (e.g., 3'-A overhangs) that complement to 3'-overhangs of sequencing adapters (e.g., 3'-T overhangs) to facilitate ligation between the DNA fragments and the sequencing adapters.

In certain other embodiments, DNA molecules from a sample also include ds DNA molecules generated from ss nucleic acids, such as cDNA molecules generated from mRNAs isolated from the sample. The cDNA molecules may also be first fragmented, the resulting fragments may be then end-repaired, and optionally single or multiple nucleotides may be added to the 3' termini of the end-repaired cDNA fragments before being ligated to sequencing adapters.

Methods for fragmenting DNA molecules, end-repairing of DNA fragments, adding 3'-overhangs to end-repaired DNA fragments, and ligating adapters to blunt-ended DNA fragments or to DNA fragments with 3'-overhangs (e.g., modified DNA molecules or fragments having adenines added to their 3' ends) are known in the art and may be used in generating sequencing libraries. Exemplary methods include those described in Sambrook J and Russell D W, editors. (2001) Molecular Cloning: A Laboratory Manual. 3rd ed. Cold Spring Harbor, NY: Cold Spring Harbor Laboratory; Son and Taylor, Curr. Protoc Microbio. February 2011, Chapter: Unit 1E.4. PMCID: PMC3076644; Qiagen GeneRead™ Library Prep (L) Handbook; Qiagen GeneRead™ Library Prep (I) Handbook; and U.S. Patent Application Publication Nos. 2010/0197509 and 2013/0005613.

The sequencing adapters ligated to the two ends of a blunt-ended nucleic acid may be the same or different. In certain embodiments, they are different. For example, one of the two adapters may carry a group (e.g., a biotin group) to facilitate the isolation of adapted nucleic acids having two different adapters. For example, two adapters, "A" and "B," are ligated to the ends of nucleic acids. Adapter "B" carries a biotin group, which facilitates the purification of homo-adapted nucleic acids (A/A or B/B). The biotin labeled sequencing library is captured on streptavidin beads. Nucleic acids containing the biotin labeled B adapter are bound to the streptavidin beads while homozygous, non biotinylated NA adapters are washed away. The immobilized nucleic acids are denatured after which both strands of the B/B adapted nucleic acids remain immobilized by the streptavidin-biotin bond and single-strand template of the NB nucleic acids are freed and used in sequencing.

Figure 7:
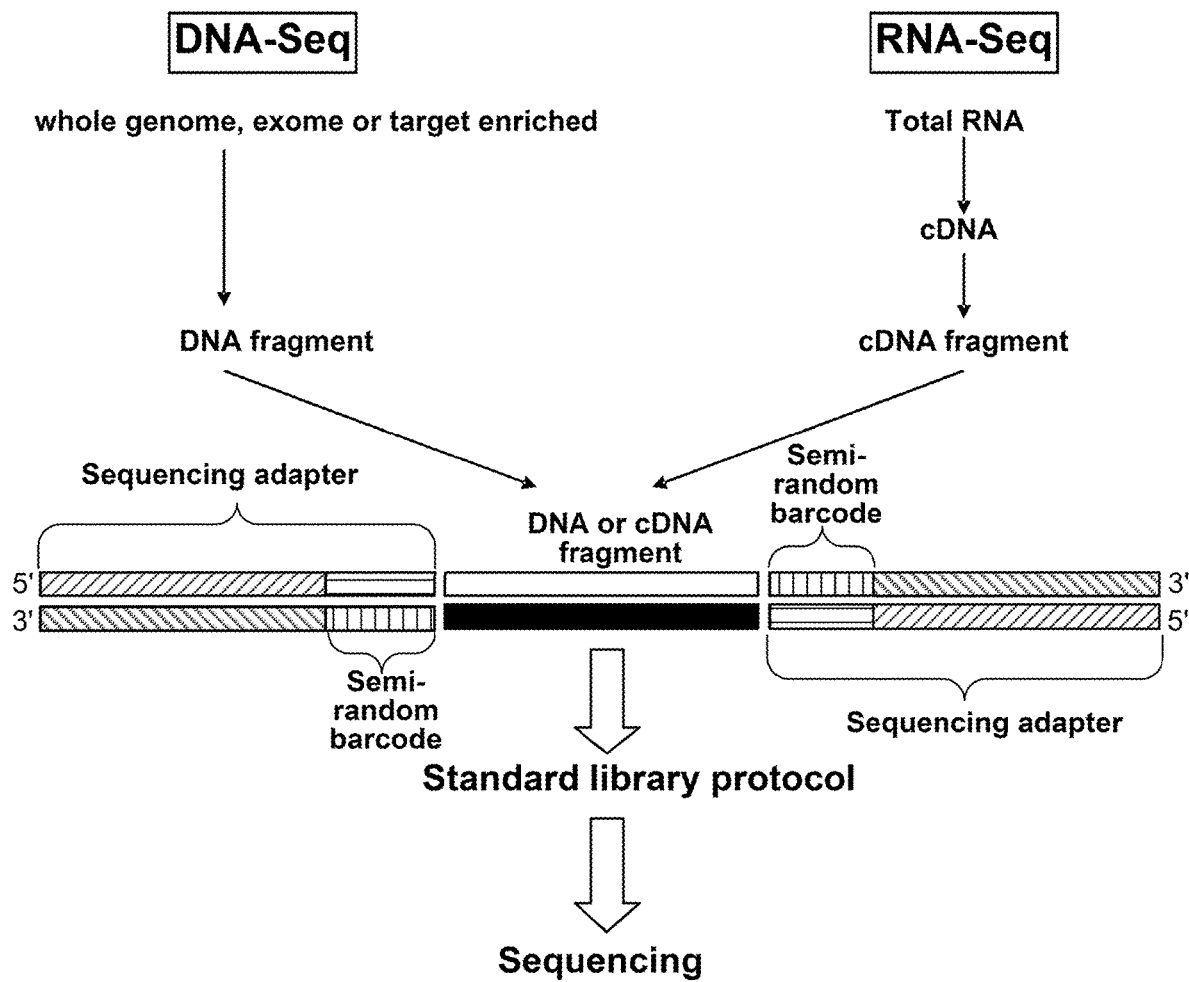
FIG. 7 is a schematic representation of a process of incorporating semi-random barcode sequences into a sequencing library and subsequent sequencing.

A schematic representation of generating a sequencing library of DNA or cDNA molecules or fragments using sequencing adapters having a semi-random barcode sequence (as well as subsequent sequencing) is shown in FIG. 7.

ii. Multiple Sets of Sequencing Adapters

In addition to preparing a sequencing library using a plurality of ds sequencing adapters (i.e., a single set of ds sequencing adapters) that comprise a semi-random barcode sequence, the present disclosure also provides a method for preparing a plurality of sequencing libraries that use a plurality of sets of ds sequencing adapters that comprise a semi-random barcode sequence provided herein. The method comprises: (1) ligating the sequencing adapters of each set to DNA fragments of each of a plurality of samples, thereby generating a plurality of sequencing libraries.

The plurality of sets of ds sequencing adapters is as described above and comprises the same $2^{nd}$ sequence and optionally the same $4^{th}$ sequence. Such common sequences among different sets of sequencing adapters allow anchoring the DNA molecules or fragments of different sequencing libraries to a solid surface for high throughput sequencing via sequences that are complementary to these common sequences and immobilized to the solid surface. Thus, the resulting plurality of sequencing libraries may first pooled together and then amplified (optionally) and sequenced together.

Also as described above, the plurality of sets of sequencing adapters have different $3^{rd}$ sequences. Such different sequences are used to tag DNA molecules or fragments of different samples.

The above descriptions of the sample from which DNA molecules or fragments are isolated and sequenced, the optional pretreatments of DNA molecules or fragments (e.g., fragmenting, end-repairing, and generating 3'-overhangs), and ligating sequencing adapters to DNA molecules or fragments in connection to the method of preparing a sequencing library using a single set of sequencing adapters are also applicable to the method of preparing multiple sequencing libraries using multiple sets of sequencing adapters and thus referred to in this section.

In certain embodiments, the DNA fragments of each sample are genomic DNA fragments. In other embodiments, the DNA fragments are cDNA molecules or fragments.

In certain embodiments, the DNA fragments of each sample are prepared by fragmenting DNAs from the sample, end repairing the fragmented DNAs, and optionally adding a single nucleotide (e.g., performing A-addition) or multiple nucleotides on end-repaired DNA fragments.

iii. Kits for Preparing Sequencing Libraries

The present disclosure also provides a kit for preparing sequencing libraries. The kit comprises sequencing adapters or sets of sequencing adapters that comprise semi-random barcode sequences as provided herein, and may further comprise one or more of the following additional components: a DNA ligase (e.g., T4 DNA ligase and *E. coli* DNA ligase), a ligation buffer, an end-repair enzyme mix (e.g., an enzyme mix containing T4 DNA polymerase coupled with Klenow DNA Polymerase and T4 Polynucleotide kinase), an end-repair buffer, a dNTP mix, an A-Addition buffer, dATP, and Klenow fragment (3'→5' exo⁻).

The kit may be used to substitute regular sequencing platform adapters with the sequencing adapters containing semi-random barcode sequences for correcting DNA or RNA counting bias and decreasing error rates associated with library preparation and sequencing process.

b. Using Reverse Transcription Primers

In a related aspect, the present disclosure also provides a method for preparing a sequencing library, comprising: (1) reverse transcribing mRNAs of a sample in the presence of the plurality of reverse transcription primers that comprise a semi-random barcode sequence as described above to generate cDNAs, and (2) attaching the cDNAs of step (1) to at least one ds sequencing adapter, thereby generating a sequencing library.

In certain embodiments, the same sequencing adapter is attached (e.g., ligated) to both ends of each cDNA molecule. In other embodiments, two different sequencing adapters are attached (e.g., ligated) to the two ends of each cDNA molecule. The ds sequencing adapter(s) used in this method do not need to contain a semi-random barcode sequence because the semi-random barcode sequence is present in the reverse transcription primer and thus already incorporated into the cDNAs prior to being ligated to the sequencing adapter(s).

In addition to the method for preparing a sequencing library using a plurality of reverse transcription primers (i.e., a single set of reverse transcription primers) that comprise a semi-random barcode sequence, the present disclosure also provides a method for preparing a plurality of sequencing libraries that use a plurality of sets of reverse transcription primers that comprise a semi-random barcode sequence. The method comprises: (1) reverse transcribing mRNAs of a plurality of samples in the presence of a plurality of sets of reverse transcription primers provided herein to generate a plurality of sets of cDNAs, and (2) ligating the plurality of sets of cDNAs of step (1) with at least one ds sequencing adapter, thereby generating a plurality of sequencing libraries.

The attachment (e.g., ligation) of cDNAs to one or more ds sequencing adapters allow anchoring the cDNAs of different sets to a solid surface for high throughput sequencing via sequences that are complementary to the sequencing adapter(s) and immobilized to the solid surface. Thus, the resulting plurality of sequencing libraries may first pooled together and then amplified (optionally) and sequenced together.

Also as described above, the plurality of sets of reverse transcription primers have different $3^{rd}$ sequences. Such different sequences are used to tag cDNA molecules or fragments of different samples.

The present disclosure also provides a kit for preparing sequencing libraries. The kit comprises reverse transcription primers or sets of reverse transcription primers that comprise semi-random barcode sequences as provided herein, and may further comprise one or more of the following additional components: a reverse transcriptase (e.g., AMV reverse transcriptase or M-MLV reverse transcriptase), a reverse transcription reaction buffer, a DNA ligase (e.g., T4 DNA ligase and *E. coli* DNA ligase), a ligation buffer, one or more adapters for a specific sequencing platform, an end-repair enzyme mix (e.g., an enzyme mix containing T4 DNA polymerase coupled with Klenow DNA Polymerase and T4 Polynucleotide kinase), an end-repair buffer, a dNTP mix, an A-Addition buffer, dATP, and Klenow fragment (3'→5' exo⁻).

In another related aspect, the present disclosure provides an alternative and preferred method for preparing a sequencing library. The method comprises a first step of reverse transcribing mRNAs of a sample to generate cDNA using a plurality of reverse transcription primers that each comprise (a) a $1^{st}$ sequence that is a semi-random barcode sequence, (b) a $2^{nd}$ sequence that comprises poly(T), (c) optionally a $3^{rd}$ sequence that may function as an index to tag a sample, and (d) a $4^{th}$ sequence that is located 5' to the $1^{st}$ sequence, the $2^{nd}$ sequence, and the $3^{rd}$ sequence (if present), as described above. The resulting cDNAs are then amplified in the presence of a primer (preferably a primer other than the reverse transcription primers) that comprises the $4^{th}$ sequence if the $4^{th}$ sequence comprises a sequencing adapter sequence, thereby generating a sequencing library. If the $4^{th}$ sequence does not itself comprise a sequencing adapter sequence, the cDNAs may be amplified in the presence of a primer that comprises, from the 3' to 5' direction, the $4^{th}$ sequence and a sequencing adapter sequence.

In the embodiments where the $4^{th}$ sequence comprises a sequencing adapter sequence, the cDNA may be amplified via PCR using a primer (other than the reverse transcription primers) that comprises the $4^{th}$ sequence and another primer ("$2^{nd}$ primer") that comprises another sequencing adapter sequence ("$2^{nd}$ sequencing adapter sequence") located 5' to a sequence complementary to a portion of the cDNA. The $2^{nd}$ sequencing adapter sequence may be the same as, but preferably different from, the sequencing adapter sequence in the $4^{th}$ sequence.

In the embodiments where the $4^{th}$ sequence does not itself comprise any sequencing adapter sequence, the cDNA may be amplified via PCR using a primer pair, one of which ("$1^{st}$ primer") comprises, from the 3' to 5' direction, the $4^{th}$ sequence and a sequencing adapter sequence. The other primer ("$2^{nd}$ primer") that comprises another sequencing adapter sequence ("$2^{nd}$ sequencing adapter sequence") located 5' to a sequence complementary to a portion of the cDNA. The $2^{nd}$ sequencing adapter sequence may be the same as, but preferably different from, the sequencing adapter sequence in the $1^{st}$ primer. In addition to the method for preparing a sequencing library using a plurality of reverse transcription primers (i.e., a single set of reverse transcription primers) that comprise a semi-random barcode sequence, the present disclosure also provides a method for preparing a plurality of sequencing libraries that use a plurality of sets of reverse transcription primers that comprise a semi-random barcode sequence. The method comprises a first step of reverse transcribing mRNAs of a plurality of samples to generate cDNA using a plurality of sets of reverse transcription primers, each reverse transcription primer comprises (a) a $1^{st}$ sequence that is a semi-random barcode sequence, (b) a $2^{nd}$ sequence that comprises poly(T), (c) a $3^{rd}$ sequence that functions as an index to tag a sample, and (d) a $4^{th}$ sequence that is located 5' to the $1^{st}$ sequence, the $2^{nd}$ sequence, and the $3^{rd}$ sequence (if present), as described above. The $3^{rd}$ sequence is the same among reverse transcription primers in a single set, but is different from that in a different set. The resulting cDNAs are then amplified in the presence of a primer (other than the reverse transcription primers) that comprises the $4^{th}$ sequence if the $4^{th}$ sequence comprises a sequencing adapter sequence, thereby generating a plurality of sequencing libraries. Otherwise, if the $4^{th}$ sequence does not itself comprise a sequencing adapter sequence, the cDNAs may be amplified in the presence of a primer that comprises, from the 3' to 5' direction, the $4^{th}$ sequence and a sequencing adapter sequence to generate a plurality of sequencing libraries.

Linking cDNAs to one or more ds sequencing adapters via PCR allow anchoring the cDNAs of different sets to a solid surface for high throughput sequencing via sequences that are complementary to the sequencing adapter(s) and immobilized to the solid surface. Thus, the resulting plurality of sequencing libraries may first pooled together and then amplified (optionally) and sequenced together.

Also as described above, the plurality of sets of reverse transcription primers have different $3^{rd}$ sequences. Such different sequences are used to tag cDNA molecules or fragments of different samples.

The present disclosure also provides a kit for preparing sequencing libraries. The kit comprises reverse transcription primers or sets of reverse transcription primers that comprise semi-random barcode sequences as provided herein, and may further comprise one or more of the following additional components: a reverse transcriptase (e.g., AMV reverse transcriptase or M-MLV reverse transcriptase), a reverse transcription reaction buffer, a DNA polymease (e.g., Taq DNA polymerase), and a PCR buffer.

c. Using PCR Primers

In a related aspect, the present disclosure also provides a method for preparing a sequencing library, comprising: (1) amplifying nucleic acids in a region of interest in a sample in the presence of the plurality of PCR primers that comprise a semi-random barcode sequence as described above to amplified DNAs, and (2) attaching (e.g., ligating) the amplified DNAs of step (1) with at least one ds sequencing adapter, thereby generating a sequencing library.

In certain embodiments, the same sequencing adapter is attached (e.g., ligated) to both ends of each amplified DNA molecule. In other embodiments, two different sequencing adapters are ligated to the two ends of each amplified DNA molecule. The ds sequencing adapter(s) used in this method do not need to contain a semi-random barcode sequence because the semi-random barcode sequence is present in the PCR primers and thus already incorporated into the amplified DNAs prior to being ligated to the sequencing adapter(s).

In addition to the method for preparing a sequencing library using a plurality of PCR primers (i.e., a single set of PCR primers) that comprise a semi-random barcode sequence, the present disclosure also provides a method for preparing a plurality of sequencing libraries that use a plurality of sets of PCR primers that comprise a semi-random barcode sequence. The method comprises: (1) amplifying nucleic acids in a region of interest in a plurality of sample in the presence of a plurality of sets of PCR primers provided herein to generate a plurality of sets of amplified DNAs, and (2) attaching (e.g., ligating) the plurality of sets of amplified DNAs of step (1) with at least one ds sequencing adapter, thereby generating a plurality of sequencing libraries.

The attachment (e.g., ligation) of amplified DNAs to one or more sequencing adapters allow anchoring the amplified DNAs of different sets to a solid surface for high throughput sequencing via sequences that are complementary to the sequencing adapter(s) and immobilized to the solid surface. Thus, the resulting plurality of sequencing libraries may first pooled together and then amplified (optionally) and sequenced together.

Also as described above, the plurality of sets of PCR primers have different $3^{rd}$ sequences. Such different sequences are used to tag DNA molecules or fragments of different samples.

The present disclosure also provides a kit for preparing sequencing library. The kit comprises PCR primers or sets of PCR primers that comprise semi-random barcode sequences as provided herein, and may further comprise one or more of the following additional components: a DNA polymerase (e.g., Taq polymerase), a PCR reaction buffer, a DNA ligase (e.g., T4 DNA ligase and *E. coli* DNA ligase), a ligation buffer, one or more adapters for a specific sequencing platform, an end-repair enzyme mix (e.g., an enzyme mix containing T4 DNA polymerase coupled with Klenow DNA Polymerase and T4 Polynucleotide kinase), an end-repair buffer, a dNTP mix, an A-Addition buffer, dATP, and Klenow fragment (3'→5' exo⁻).

In another related aspect, the present disclosure provides alternative and preferred methods for preparing a sequencing library. One method comprises amplifying nucleic acids in a region of interest in a sample in the presence of a plurality of PCR primers ("$1^{st}$ primers") that each comprise (a) a $1^{st}$ sequence that is a semi-random barcode sequence, (b) a $2^{nd}$ sequence that is fully or substantially complementary to a conserved sequence of the region of interest, (c) optionally a $3^{rd}$ sequence that may function as an index to tag a sample, and (d) a $4^{th}$ sequence that is located 5' to the $1^{st}$ sequence, the $2^{nd}$ sequence, and the $3^{rd}$ sequence (if present), and comprises a sequencing adapter sequence as described above.

In such a method, another primer ("$2^{nd}$ primer") that comprises another sequencing adapter sequence ("$2^{nd}$ sequencing adapter sequence") located 5' to a sequence complementary to a portion of the nucleic acids in the region of interest is also used. The $2^{nd}$ sequencing adapter sequence may be the same as, but preferably different from, the sequencing adapter sequence in the $4^{th}$ sequence.

An alternative method is also provided using a plurality of PCR primers ("$1^{st}$ primers") that each comprise (a) a $1^{st}$ sequence that is a semi-random barcode sequence, (b) a $2^{nd}$ sequence that is fully or substantially complementary to a conserved sequence of the region of interest, (c) optionally a $3^{rd}$ sequence that may function as an index to tag a sample, and (d) a $4^{th}$ sequence that is located 5' to the $1^{st}$ sequence, the $2^{nd}$ sequence, and the $3^{rd}$ sequence (if present), but does not comprise a sequencing adapter sequence as described above.

Such a method comprises: (1) amplifying nucleic acids in a region of interest in a sample in the presence of the plurality of such PCR primers to generate amplified nucleic acids, and (2) further amplifying the amplified nucleic acids in the presence of a primer ("$3^{rd}$ primer") that comprises from the 3' to 5' direction, the $4^{th}$ sequence and a sequencing adapter sequence, thereby generating a sequencing library.

In the $1^{st}$ amplification step, in addition to the plurality of the $1^{st}$ primers, a $2^{nd}$ primer at least partially complementary to a portion of the nucleic acids in the region of interest is also used. The $2^{nd}$ primer may or may not comprise another sequencing adapter sequence ("$2^{nd}$ sequencing adapter sequence") located 5' to a sequence complementary to a portion of the nucleic acids. The $2^{nd}$ sequencing adapter sequence may be the same as, but preferably different from, the sequencing adapter sequence in the primer that comprises the $4^{th}$ sequence used during the $2^{nd}$ amplification step.

Preferably, the PCR during the $1^{st}$ amplification step should only be performed for a few cycles of primer extension (e.g., 2, 3, 4, 5, and most preferably 2) to minimize the risk that the same nucleic acid is labeled with multiple semi-random barcode sequences.

In the $2^{nd}$ amplification step, in addition to the $3^{rd}$ primer that comprises, from the 3' to 5' direction, the $4^{th}$ sequence and a sequencing adapter sequence, a $4^{th}$ primer is also used. If the $2^{nd}$ primer in the $1^{st}$ amplification step comprises a $2^{nd}$ sequencing adapter sequence, it may be used as the $4^{th}$ primer in the $2^{nd}$ amplification step as well. However, if the $2^{nd}$ primer in the $1^{st}$ amplification step does not comprise any sequencing adapter sequence, the $4^{th}$ primer of the $2^{nd}$ amplification step will comprise a sequencing adapter sequence, which may or may not be the same as the sequencing adapter sequence of the sequencing adapter sequence in the $3^{rd}$ primer.

In addition to the method for preparing a sequencing library using a plurality of PCR primers (i.e., a single set of PCR primers) that comprise a semi-random barcode sequence, the present disclosure also provides methods for preparing a plurality of sequencing libraries that use a plurality of sets of PCR primers that comprise a semi-random barcode sequence.

One method comprises amplifying nucleic acids in a region of interest in a sample in the presence of a plurality of sets of PCR primers that each comprise (a) a $1^{st}$ sequence that is a semi-random barcode sequence, (b) a $2^{nd}$ sequence that is fully or substantially complementary to a conserved sequence of the region of interest, (c) a $3^{rd}$ sequence that may function as an index to tag a sample, and (d) a $4^{th}$ sequence that is located 5' to the $1^{st}$ sequence, the $2^{nd}$ sequence, and the $3^{rd}$ sequence, and comprises a sequencing adapter sequence as described above.

An alternative method is also provided using a plurality of sets of PCR primers that each comprise (a) a $1^{st}$ sequence that is a semi-random barcode sequence, (b) a $2^{nd}$ sequence that is fully or substantially complementary to a conserved sequence of the region of interest, (c) a $3^{rd}$ sequence that may function as an index to tag a sample, and (d) a $4^{th}$ sequence that is located 5' to the $1^{st}$ sequence, the $2^{nd}$ sequence, and the $3^{rd}$ sequence, but does not comprise a sequencing adapter sequence as described above.

Such a method comprises: (1) amplifying nucleic acids in a region of interest in a plurality of samples in the presence of the plurality of sets of such PCR primers to generate amplified nucleic acids, and (2) further amplifying the amplified nucleic acids in the presence of a primer that comprises from the 3' to 5' direction, the $4^{th}$ sequence and a sequencing adapter sequence, thereby generating multiple sequencing libraries.

Linking nucleic acids in a region of interest of multiple samples to one or more ds sequencing adapters via PCR allow anchoring the nucleic acids from different sample to a solid surface for high throughput sequencing via sequences that are complementary to the sequencing adapter(s) and immobilized to the solid surface. Thus, the resulting plurality of sequencing libraries may first pooled together and then amplified (optionally) and sequenced together.

Also as described above, the plurality of sets of PCR primers have different $3^{rd}$ sequences. Such different sequences are used to tag nucleic acid molecules or fragments of different samples.

The present disclosure also provides a kit for preparing sequencing libraries. The kit comprises PCR primers or sets of PCR primers that comprise semi-random barcode sequences as provided herein, and may further comprise one or more of the following additional components: a DNA polymerase (e.g., Taq DNA polymerase), and a PCR buffer.

d. Using Single-Stranded Oligonucleotides for Sequencing Single-Stranded Nucleic Acids The present disclosure also provides methods for preparing a sequencing library using ss oligonucleotides for sequencing ss nucleic acids from a sample.

Single-stranded nucleic acids from a sample that may be sequenced by the method provided herein include any ss nucleic acids. Preferably, the ss nucleic acids are microRNAs (miRNAs). miRNAs are a family of small ribonucleic acids, typically 21-25 nucleotides in length, that modulate protein expression through various mechanisms, such as transcript degradation, inhibition of translation, or sequestering transcripts.

miRNAs may be isolated by methods known in the art, such as isolating total RNA followed by size fractionation of small RNAs by gel electrophoresis.

(i) $1^{st}$ Arrangement

One method comprises the use of a plurality of ss oligonucleotides that each comprise: (a) a $1^{st}$ sequence that is a semi-random sequence consisting of $(Xmer)_n$, (b) optionally a $2^{nd}$ sequence that (i) has a defined sequence that is 3 to 8 nucleotides in length, and (ii) is the same among the oligonucleotides, and (c) a $3^{rd}$ sequence that (i) has a defined sequence, (ii) is the same among the oligonucleotides, and (iii) is located 5' to the $1^{st}$ sequence and the $2^{nd}$ sequence (if present).

In certain embodiments, the method comprises: (1) ligating the plurality of ss oligonucleotides to the 5' termini of ss nucleic acids of a sample, and (2) amplifying the ss nucleic acids (a) in the presence of a primer comprising the $3^{rd}$ sequence if the $3^{rd}$ sequence comprises a sequencing adapter sequence, or (b) in the presence of a primer comprising, from the 3' to 5' direction, the $3^{rd}$ sequence and a sequencing adapter sequence, if the $3^{rd}$ sequence does not comprise a sequencing adapter sequence.

The ligation step adds ss oligonucleotides to the 5' termini of ss nucleic acids of a sample and may be performed by a method known in the art using a ligase, such as T4 RNA ligase 2.

The amplification step is performed in the presence of a PCR primer pair, one of which ("$1^{st}$ primer") comprises the $3^{rd}$ sequence in the ss oligonucleotides. If the $3^{rd}$ sequence contains a sequencing adapter sequence ("$1^{st}$ sequencing adapter sequence"), then the $1^{st}$ primer may (but is not required to) comprise the $3^{rd}$ sequence without an additional sequence. However, if the $3^{rd}$ sequence does not contain a sequencing adapter sequence, then the $1^{st}$ primer comprises, in addition to the $3^{rd}$ sequence, a sequencing adapter sequence located 5' to the $3^{rd}$ sequence.

In addition to the primer that comprises the $3^{rd}$ sequence, the amplification step is performed in the presence of another primer ("$2^{nd}$ primer"). The $2^{nd}$ primer comprises, from the 3' to 5' direction, a sequence complementary to the ss nucleic acids of the sample and another sequencing adapter sequence ("$2^{nd}$ sequencing adapter sequence"). The sequence complementary to ss nucleic acids of the sample allows the $2^{nd}$ primer to anneal to the ss nucleic acids for primer extension using the ss nucleic acids as templates during PCR. The $2^{nd}$ sequencing adapter sequence may be the same as, but preferably different from, the $1^{st}$ sequencing adapter.

The amplification may be performed using a DNA polymerase with reverse transcriptase (i.e., RNA-dependent DNA polymerase) activity so that primer extension may be performed using both RNA and DNA as a template. Alternatively, the amplification may be performed using a reverse transcriptase and a DNA-dependent DNA polymerase.

In certain other related embodiments, the method comprises: (1) ligating the plurality of ss oligonucleotides ("5' ligation adapters") to the 5' termini of ss nucleic acids of a sample, (2) ligating another ss oligonucleotide ("3' ligation adapater") to the 3' termini of ss nucleic acids of the sample, and (3) amplifying the ss nucleic acids of the sample (a) in the presence of a primer comprising the $3^{rd}$ sequence if the $3^{rd}$ sequence comprises a sequencing adapter sequence, or (b) in the presence of a primer comprising, from the 3' to 5' direction, the $3^{rd}$ sequence and a sequencing adapter sequence, if the $3^{rd}$ sequence does not comprise a sequencing adapter sequence.

The steps of ligating the 5' ligation adapters to the 5' termini of ss nucleic acids of a sample and ligating the 3' ligation adapter to the 3' termini of ss nucleic acids of the sample may be performed by a method known in the art using a ligase, such as T4 RNA ligase 2.

The 3' ligation adapter may or may not comprise a sequencing adapter sequence. If present, the sequencing adapter sequence in the 3' ligation adapter may be the same but preferably different from the sequencing adapter sequence in the 5' ligation adapters.

The amplification step is performed in the presence of a PCR primer pair, one of which ("$1^{st}$ primer") comprises the $3^{rd}$ sequence in the ss oligonucleotides. If the $3^{rd}$ sequence contains a sequencing adapter sequence ("$1^{st}$ sequencing adapter sequence"), then the $1^{st}$ primer may (but is not required to) comprise the $3^{rd}$ sequence without an additional sequence. However, if the $3^{rd}$ sequence does not contain a sequencing adapter sequence, then the $1^{st}$ primer comprises, in addition to the $3^{rd}$ sequence, a sequencing adapter sequence located 5' to the $3^{rd}$ sequence.

In addition to the primer that comprises the $3^{rd}$ sequence, the amplification step is performed in the presence of another primer ("$2^{nd}$ primer"). If the 3' ligation adapter already comprises a sequencing adapter sequence, the $2^{nd}$ primer may comprise a sequence fully or substantially complementary to the sequencing adapter sequence or a portion thereof in the 3' ligation adapter. If the 3' ligation adapter does not comprise any sequencing adapter sequence, the $2^{nd}$ primer may comprise, from the 3' to 5' direction, a sequence complementary to the sequence of the 3' ligation adapter and another sequencing adapter sequence ("$2^{nd}$ sequencing adapter sequence") The $2^{nd}$ sequencing adapter sequence may be the same as, but preferably different from, the sequencing adapter sequence in the 5' ligation adapter or in the $1^{st}$ primer.

The amplification may be performed using a DNA polymerase with reverse transcriptase (i.e., RNA-dependent DNA polymerase) activity so that primer extension may be performed using both RNA and DNA as a template. Alternatively, the amplification may be performed using a reverse transcriptase and a DNA-dependent DNA polymerase.

In addition to the methods for preparing a sequencing library using a plurality of ss oligonucleotides (i.e., a single set of ss oligonucleotides) that comprise a semi-random barcode sequence, the present disclosure also provides a method for preparing a plurality of sequencing libraries that use a plurality of sets of ss oligonucleotides that comprise a semi-random barcode sequence. The method comprises: (1) ligating the plurality of sets of ss oligonucleotides to the 5' termini of ss nucleic acids of a sample, wherein each of the ss oligonucleotides comprises a $2^{nd}$ sequence that (i) has a defined sequence that is 3 to 8 nucleotides in length, and (ii) is the same among the oligonucleotides of the same set, but different among the oligonucleotides of different sets, and (2) amplifying the ss nucleic acids (a) in the presence of a primer comprising the $3^{rd}$ sequence if the $3^{rd}$ sequence comprises a sequencing adapter sequence, or (b) in the presence of a primer comprising, from the 3' to 5' direction, the $3^{rd}$ sequence and a sequencing adapter sequence, if the $3^{rd}$ sequence does not comprise a sequencing adapter sequence.

As described above, the plurality of sets of ss oligonucleotides have different $2^{nd}$ sequences. Such different sequences may be used to tag ss nucleic acids of different samples. However, because the sequencing libraries generated for ss nucleic acids of different samples contain the same one or more sequencing adapters, such libraries may be attached to a solid surface for high throughput sequencing via sequences that are complementary to the sequencing adapter(s) and immobilized to the solid surface. Thus, the plurality of sequencing libraries may first pooled together and then amplified (optionally) and sequenced together.

The present disclosure also provides a kit for preparing sequencing library. The kit comprises ss oligonucleotides or sets of ss oligonucleotides that comprise semi-random barcode sequences as provided herein, and may further comprise one or more of the following additional components: a DNA polymerase, a PCR reaction buffer, a ligase (e.g., a RNA ligase, such as T4 RNA ligase 2), and a ligation buffer.

(ii) 2$^{nd}$ Arrangement

One method comprises the use of a plurality of ss oligonucleotides that each comprise: (a) a 1$^{st}$ sequence that is a semi-random sequence consisting of (Xmer)n, (b) optionally a 2$^{nd}$ sequence that (i) has a defined sequence that is 3 to 8 nucleotides in length, and (ii) is the same among the oligonucleotides, and (c) a 3$^{rd}$ sequence that (i) has a defined sequence, (ii) is the same among the oligonucleotides, and (iii) is located 3' to the 1$^{st}$ sequence and the 2$^{nd}$ sequence (if present).

In certain embodiments, the method comprises: (1) ligating the plurality of ss oligonucleotides to the 3' termini of ss nucleic acids of a sample, and (2) amplifying the ss nucleic acids (a) in the presence of a primer comprising a sequence at least substantially complementary to the 3$^{rd}$ sequence if the 3$^{rd}$ sequence comprises a sequencing adapter sequence, or (b) in the presence of a primer comprising, from the 3' to 5' direction, a sequence at least substantially complementary to the 3$^{rd}$ sequence and a sequencing adapter sequence if the 3$^{rd}$ sequence does not comprise a sequencing adapter sequence.

A sequence "at least substantially complementary to the 3$^{rd}$ sequence" if a primer comprising such a sequence is able to specifically anneal to the 3$^{rd}$ sequence to allow primer extension. The sequence at least substantially complementary to the 3$^{rd}$ sequence may have at least 85%, at least 90%, at least 95%, at least 98%, or 100% of its residues complementary to residues at corresponding positions of the 3$^{rd}$ sequence.

The ligation step adds ss oligonucleotides to the 3' termini of ss nucleic acids of a sample and may be performed by a method known in the art.

The amplification step is performed in the presence of a PCR primer pair, one of which ("1$^{st}$ primer") comprises a sequence at least substantially complementary to the 3$^{rd}$ sequence in the ss oligonucleotides. If the 3$^{rd}$ sequence contains a sequencing adapter sequence ("1$^{st}$ sequencing adapter sequence"), then the 1$^{st}$ primer may (but is not required to) comprise a sequence at least substantially complementary to the 3$^{rd}$ sequence without an additional sequence. However, if the 3$^{rd}$ sequence does not contain a sequencing adapter sequence, then the 1$^{st}$ primer comprises, in addition to a sequence at least substantially complementary to the 3$^{rd}$ sequence, a sequencing adapter sequence located 5' to the sequence at least substantially complementary to the 3$^{rd}$ sequence. The extension of the 1$^{st}$ primer using the ligation products of the ss nucleic acids of a sample and the plurality of ss oligonucleotides as described above produces extension products ("1$^{st}$ extension products") that comprise the complementary sequences of the ss nucleic acids of the sample.

In addition to the primer that comprises a sequence at least substantially complementary to the 3$^{rd}$ sequence, the amplification step is performed in the presence of another primer ("2$^{nd}$ primer"). The 2$^{nd}$ primer comprises, from the 3' to 5' direction, a sequence identical or substantially homologous to a portion of one or more ss nucleic acids of the sample and another sequencing adapter sequence ("2$^{nd}$ sequencing adapter sequence"). The sequence identical or substantially homologous to the ss nucleic acid(s) of the sample in the 2$^{nd}$ primer allows the 2$^{nd}$ primer to anneal to the above-described 1$^{st}$ extension products and to extend using the 1$^{st}$ extension product as templates during PCR. The 2$^{nd}$ sequencing adapter sequence may be the same as, but preferably different from, the 1$^{st}$ sequencing adapter.

The amplification may be performed using a DNA polymerase with reverse transcriptase (i.e., RNA-dependent DNA polymerase) activity so that primer extension may be performed using both RNA and DNA as a template. Alternatively, the amplification may be performed using a reverse transcriptase and a DNA-dependent DNA polymerase.

In certain other related embodiments, the method comprises: (1) ligating the plurality of ss oligonucleotides ("3' ligation adapters") to the 3' termini of ss nucleic acids of a sample, (2) ligating another ss oligonucleotide ("5' ligation adapter") to the 5' termini of ss nucleic acid of the sample, and (3) amplifying the ss nucleic acids of the sample (a) in the presence of a primer comprising a sequence at least substantially complementary to the 3$^{rd}$ sequence if the 3$^{rd}$ sequence comprises a sequencing adapter sequence, or (b) in the presence of a primer comprising, from the 3' to 5' direction, a sequence at least substantially complementary to the 3$^{rd}$ sequence and a sequencing adapter sequence if the 3$^{rd}$ sequence does not comprise a sequencing adapter sequence.

A sequence is "at least substantially complementary to the 3$^{rd}$ sequence" if a primer comprising such a sequence is able to specifically anneal to the 3$^{rd}$ sequence to allow primer extension. The sequence at least substantially complementary to the 3$^{rd}$ sequence may have at least 85%, at least 90%, at least 95%, at least 98%, or 100% of its residues complementary to residues at corresponding positions of the 3$^{rd}$ sequence.

The steps of ligating the 3' ligation adapters to the 3' termini of ss nucleic acids of a sample and ligating the 5' ligation adapter to the 5' termini of ss nucleic acids of the sample may be performed by a method known in the art. The 5' ligation adapter may or may not comprise a sequencing adapter sequence. If present, the sequencing adapter sequence in the 5' ligation adapter may be the same but preferably different from the sequencing adapter sequence in the 3' ligation adapters.

The amplification step is performed in the presence of a PCR primer pair, one of which ("1$^{st}$ primer") comprises a sequence at least substantially complementary to the 3$^{rd}$ sequence in the ss oligonucleotides. If the 3$^{rd}$ sequence contains a sequencing adapter sequence ("1$^{st}$ sequencing adapter sequence"), then the 1$^{st}$ primer may (but is not required to) comprise a sequence at least substantially complementary to the 3$^{rd}$ sequence without an additional sequence. However, if the 3$^{rd}$ sequence does not contain a sequencing adapter sequence, then the 1$^{st}$ primer comprises, in addition to a sequence at least substantially complementary to the 3$^{rd}$ sequence, a sequencing adapter sequence located 5' to the sequence at least substantially complementary to the 3$^{rd}$ sequence.

In addition to the primer that comprises a sequence at least substantially complementary to the 3$^{rd}$ sequence, the amplification step is performed in the presence of another primer ("2$^{nd}$ primer"). If the 5' ligation adapter already comprises a sequencing adapter sequence, the 2$^{nd}$ primer may (but is not required to) comprise the sequencing adapter sequence in the 5' ligation adapter. If the 5' ligation adapter does not comprise any sequencing adapter sequence, then the 2$^{nd}$ primer comprises, from the 3' to 5' direction, the sequence of the 5' ligation adapter or a portion thereof and another sequencing adapter sequence ("2$^{nd}$ sequencing adapter sequence"). The 2$^{nd}$ sequencing adapter sequence may be the same as, but preferably different from, the sequencing adapter sequence in the 3' ligation adapter or in the 1$^{st}$ primer.

The amplification may be performed using a DNA polymerase with reverse transcriptase (i.e., RNA-dependent DNA polymerase) activity so that primer extension may be performed using both RNA and DNA as a template. Alternatively, the amplification may be performed using a reverse transcriptase and a DNA-dependent DNA polymerase.

In addition to the method for preparing a sequencing library using a plurality of ss oligonucleotides (i.e., a single set of ss oligonucleotides) that comprise a semi-random barcode sequence, the present disclosure also provides a method for preparing a plurality of sequencing libraries that use a plurality of sets of ss oligonucleotides that comprise a semi-random barcode sequence. The method comprises: (1) ligating the plurality of sets of ss oligonucleotides to the 3' termini of ss nucleic acids of a sample, wherein each of the ss oligonucleotides comprises a $2^{nd}$ sequence that (i) has a defined sequence that is 3 to 8 nucleotides in length, and (ii) is the same among the oligonucleotides of the same set, but different among the oligonucleotides of different sets, and (2) amplifying the ss nucleic acids (a) in the presence of a primer comprising a sequence at least substantially complementary to the $3^{rd}$ sequence if the $3^{rd}$ sequence comprises a sequencing adapter sequence, or (b) in the presence of a primer comprising, from the 3' to 5' direction, a sequence at least substantially complementary to the $3^{rd}$ sequence and a sequencing adapter sequence.

As described above, the plurality of sets of ss oligonucleotides have different $2^{nd}$ sequences. Such different sequences may be used to tag ss nucleic acids of different samples. However, because the sequencing libraries generated for ss nucleic acids of different samples contain the same one or more sequencing adapters, such libraries may be attached to a solid surface for high throughput sequencing via sequences that are complementary to the sequencing adapter(s) and immobilized to the solid surface. Thus, the plurality of sequencing libraries may first pooled together and then amplified (optionally) and sequenced together.

The present disclosure also provides a kit for preparing sequencing library. The kit comprises ss oligonucleotides or sets of ss oligonucleotides that comprise semi-random barcode sequences as provided herein, and may further comprise one or more of the following additional components: a DNA polymerase, a PCR reaction buffer, a ligase (e.g., a RNA ligase), and a ligation buffer.

2. Amplifying Sequencing Libraries

A sequencing library may be first amplified before being sequenced. A plurality of sequencing libraries generated as described above may be first combined together before being amplified. Thus, the method for preparing a sequencing library or a plurality of sequencing libraries may further comprise amplifying the sequencing library or libraries.

Amplification of sequencing libraries may be performed in situ, in emulsion or in solution, including bridge PCR and emulsion PCR. Alternatively, the sequence library may directly be sequenced without amplification.

Bridge PCR amplifies DNA fragments flanked with adapters (see, U.S. Pat. No. 5,641,658). A flat surface coated with two types of primers, corresponding to the adapters. Amplification proceeds in cycles, with one end of each bridge tethered to the surface to form DNA colonies or DNA clusters.

Emulsion PCR isolates individual DNA molecules along with primer-coated beads in aqueous droplets within an oil phase (see, Williams et al., Nature Methods 3:545-50, 2006). A polymerase chain reaction then coats each bead with clonal copies of the DNA molecule.

3. Sequencing

The method for preparing a sequencing library or a plurality of sequencing libraries may further comprise sequencing the DNA molecules or fragments of a sample or a plurality of samples contained in the sequencing library or libraries.

Any high throughput sequencing platforms known in the art may be used to sequence the sequencing libraries prepared as described herein (see, Myllykangas et al., *Bioinformatics for High Throughput Sequencing*, Rodriguez-Ezpeleta et al. (eds.), Springer Science+Business Media, LLC, 2012, pages 11-25). Exemplary high throughput DNA sequencing systems include, but are not limited to, the GS FLX sequencing system originally developed by 454 Life Sciences and later acquired by Roche (Basel, Switzerland), Genome Analyzer developed by Solexa and later acquired by Illumina Inc. (San Diego, CA) (see, Bentley, Curr Opin Genet Dev 16:545-52, 2006; Bentley et al., Nature 456:53-59, 2008), the SOLiD sequence system by Life Technologies (Foster City, CA) (see, Smith et al., Nucleic Acid Res 38: e142, 2010; Valouev et al., Genome Res 18:1051-63, 2008), CGA developed by Complete Genomics and acquired by BGI (see, Drmanac et al., Science 327:78-81, 2010), PacBio RS sequencing technology developed by Pacific Biosciences (Menlo Park, CA) (see, Eid et al., Science 323: 133-8, 2009), and Ion Torrent developed by Life Technologies Corporation (see, U.S. Patent Application Publication Nos. 2009/0026082; 2010/0137143; and 2010/0282617).

During data analysis, certain errors in semi-barcode sequences in sequence reads may be corrected. For example, in certain embodiments, the semi-random sequence consisting of trimers selected from a pool of trimers where any two trimers in the pool have at least 2 nucleotide differences. This avoids the scenario where one base sequencing or polymerase error will convert one trimer into another trimer used in the same pool. For instance, if AAA and GGG are in the pool of trimers, but ATA is obtained in a sequence read, it can be determine that ATA are highly likely to come from AAA due to a sequencing error in the middle base. Thus, ATA may be corrected back to AAA in the downstream analysis.

During data analysis, sequence reads may be sorted based on the semi-barcode sequences, and reads that contain the same semi-barcode sequence may be compared. Such comparisons allow corrections of sequencing errors and thus improve sequencing accuracy, including DNA or RNA counting and mutation detection.

In certain embodiments, the method for preparing a sequencing library or a plurality of sequencing libraries provided herein further comprises determining the copy numbers of one or more sequences of interest in DNA molecules or fragments contained in the sequencing library or libraries. Instead of counting the reads of a DNA fragment (e.g., a genomic DNA fragment or a cDNA fragment) in conventional sequencing experiment, the number of different barcode families for a particular fragment is counted. The numbers of different barcode families correspond to the original numbers of the DNA fragment, and are not affected by bias or errors introduced during PCR amplification or sequencing process.

In certain embodiments, the method for preparing a sequencing library or a plurality of sequencing libraries provided herein further comprises identifying one or more genetic variations in DNA molecules or fragments contained in the sequencing library or libraries. A genetic variation is identified if it exists in the majority (e.g., at least 60%, 65, 70%, 75%, 80%, 85%, 90%, or 95%) of fragments within a barcode family (i.e., sequence reads that contain the same barcode sequence). This minimizes errors in mutation detection due to mistakes occurred in a minority of fragments within a barcode family during amplification and/or sequencing process.

Sequence reads may be sorted based on index sequences contained if the sequencing libraries are prepared using sequencing adapters, reverse transcription primers or PCR primers that comprise index sequences. The presence of such index sequences allows multiplex sequencing of DNA molecules or fragments from multiple samples.

4. Various Applications

The method for preparing a sequencing library or a plurality of sequencing libraries provided herein is useful in any application where NGS is used, including de novo genome sequencing, targeted re-sequencing (e.g., targeted re-sequencing of tumors), epigenetic studies, genetic pathogen diversity analysis, and trascriptome profiling. In addition, NGS has been used in a variety of fields including metagenomics, paleogenomics, forensics, and human genetics to analyze subpopulations in complex biological samples. Clinical applications include prenatal screening for fetal aneuploidy, early detection of cancer, monitoring patients' response to therapy, and predicting treatment efficacy in individual patients.

In certain embodiments, the method for preparing a sequencing library using a PCR primer that contains a $1^{st}$ semi-random barcode sequence and a $2^{nd}$ sequence at least substantially complementary to a conserved region of the bacterial 16S rRNA gene is used for microbial sequencing. 16S rRNA gene sequencing has a wide range of uses, including the characterization of bacteria populations, taxonomical analysis, and species identification.

The following examples are for illustration and are not limiting.

Example 1

Construct Semi-Random Barcode Adapter for Illumina Sequencing Platform

The trimer mix that contains 8 trimers (AAC, ACT, ATG, CAG, CGT, GAA, GTT, TGC) was purchased from Glen Research Corporation (Sterling, Virginia). All oligonucleotides were synthesized by Integrated DNA Technologies (Coralville, Iowa).

```
Barcoded Illumina Strand (Semi-Random):
                                        (SEQ ID NO: 21)
5'-Phos/GATC/iTriMix//iTriMix//iTriMix//iTriMix/

AGATCGGAAGAGCACACGTC*T-3'
```

"Phos" refers to a 5' phosphate group. "iTriMix" refers to one of the 8 trimers.

```
Illumina Fill-In Primer:
                                        (SEQ ID NO: 22)
5'-AATGATACGGCGACCACCGAGATCTACACTCTTTCCCTACACGA

CGCTCTTCCGAT*C*T-3'
```

* denotes a phosphorothioate bond

The following is the protocol for construction of semi-random barcode adapter for Illumina sequencing:
Strand Annealing and Primer Extension
1) Dilute Klenow Large Fragment Enzyme (NEB M0210S) to working concentration of 0.4 U/uL using 1×NEB Buffer 2
2) Set up the following strand annealing/primer extension reaction on ice:

| Component | 1 Reaction (uL) |
| --- | --- |
| dH₂0 | 2 |
| NEBuffer 2 (10X) | 2 |
| dNTPs (5 mM) | 2 |
| Barcoded Illumina Strand (200 uM) | 3 |
| Illumina Fill-In Primer (100 uM) | 6 |
| Total Volume | 15 |

3) Incubate the reaction at 95° C. for 10 mins. Reduce the temperature of the sample to 25° C. by decreasing the temperature 5° C. every 5 minutes.
4) Once sample has reached 25° C. add 5 uL of 0.4 U/uL Klenow Large Fragment Enzyme and incubate at 25° C. for 15 minutes. Cool sample to 4° C.
5) Purify sample using Qiagen MinElute PCR Purification Kit and protocol.
T-overhang Addition to Adapter
1) Dilute dTTP (Thermo Scientific R0171) to working concentration of 15 mM.
2) Set up the following T-addition reaction on ice:

| Component | 1 Reaction (uL) |
| --- | --- |
| Annealing/Extension Reaction | 4 |
| NEBuffer 2 (10X) | 2 |
| dH20 | 7 |
| Klenow (3'-5' exo-) [5U/uL] | 5 |
| dTTP (15 mM) | 2 |
| Total Volume | 20 |

3) Incubate the reaction at 37° C. for 60 minutes.
4) Purify samples using Qiagen MinElute PCR Purification Kit and protocol.

Example 2

Evaluating the Diversity of Synthesized Semi-Random Barcodes Through NGS

An ACTB amplicon was used as the template in library construction using semi-random barcode adapters. The ACTB amplicon was generated by PCR using a pair of ACTB specific primers and human cDNA. The purified amplicon was then used as the template in constructing NGS libraries following QIAGEN GeneRead DNA library Prep kit for Illumina, except that semi-random adapter was used instead of regular adapters.

First, the end-repair was done using 200 ng purified ACTB amplicon, 10× end-repair buffer and 2 ul end-repair enzyme mix in a 25 ul reaction. After incubation at 25° C. for 30 minutes and at 75° C. for 25 minutes, 3 ul A-addition buffer together with 3 ul Klenow fragment (3'-5' exo-) were added to the tube. The reaction was further incubated at 37° C. for 30 minutes, then at 75° C. for 10 minutes. Then 45 ul 2× ligation buffer, 2.5 ul of 48 uM semi-random barcode adapters, 4 ul T4 DNA ligase and water were added to make a 90 ul reaction. The reaction was incubated at 25° C. for 10 minutes, and then purified using QIAGEN GeneRead Size Selection Kit.

The purified ligation product was further amplified using Illumina_F primer and index primer included in the GeneRead DNA library Prep kit for Illumina, following the kit protocol. The amplified library was purified using QIAGEN MinElute PCR purification kit, quantified using GeneRead Library Quantification kit.

The quantified ACTB library was sequenced on MiSeq following manufacturer's instruction. The following custom MiSeq sequencing primers were used (5'-ACACTCTTTCCCTACACGACGCTCTTCCGAT-3' (SEQ ID NO: 23) and 5'-GTGACTCGAGTTCA-GACGTGTGCTCTTCCGAT-3' (SEQ ID NO: 24)).

Figure 8:
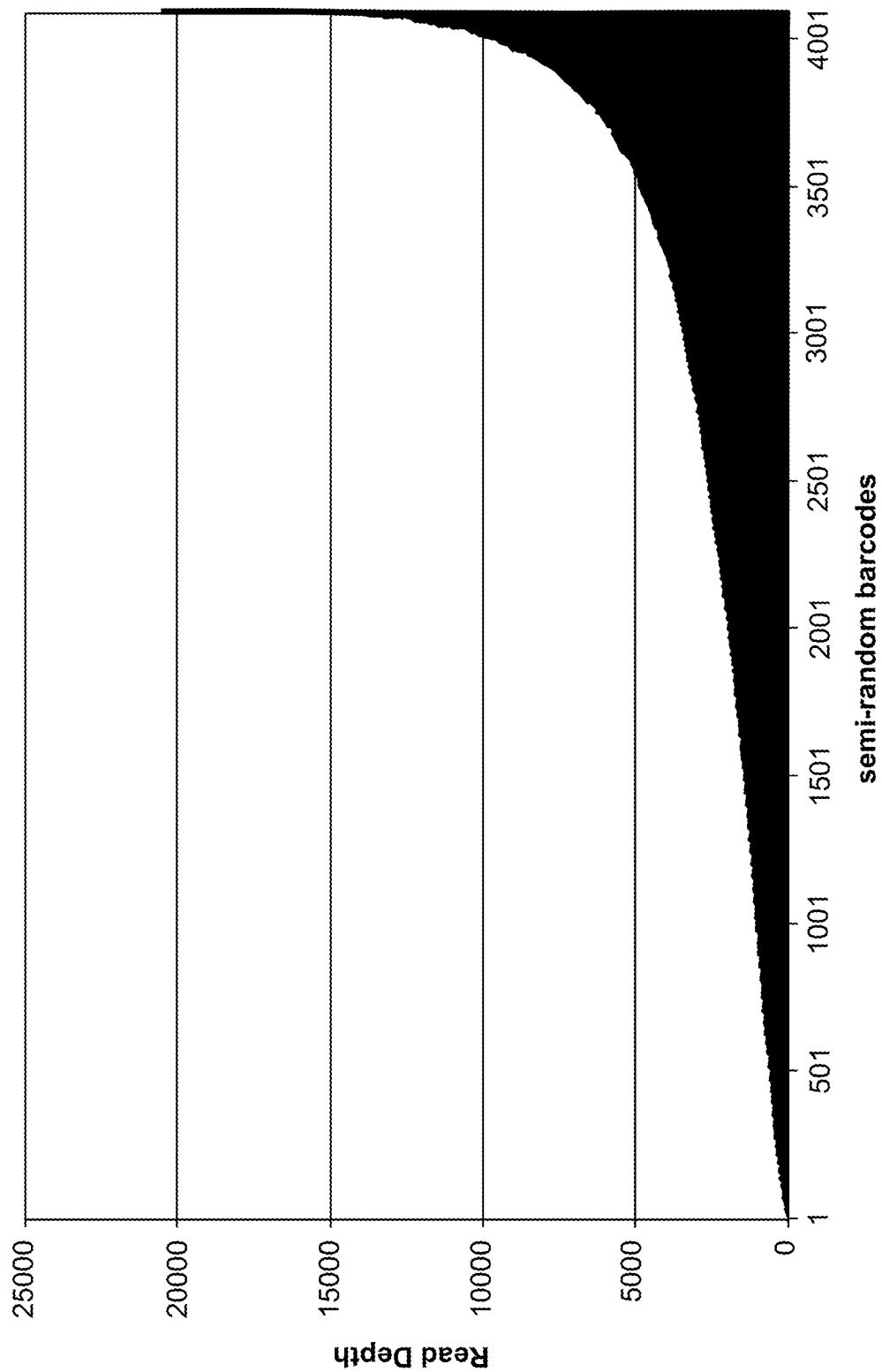
FIG. 8 is a graph showing read counts for each unique barcode as studied in Example 2.

From sequencing semi-random barcodes, all combination of semi-random trimer blocks (4096 total combinations from 8 trimer for each barcode region, and each library construct has two such regions on both sides) were observed. The read counts for each unique barcode is shown in FIG. 8.

Figure 9:
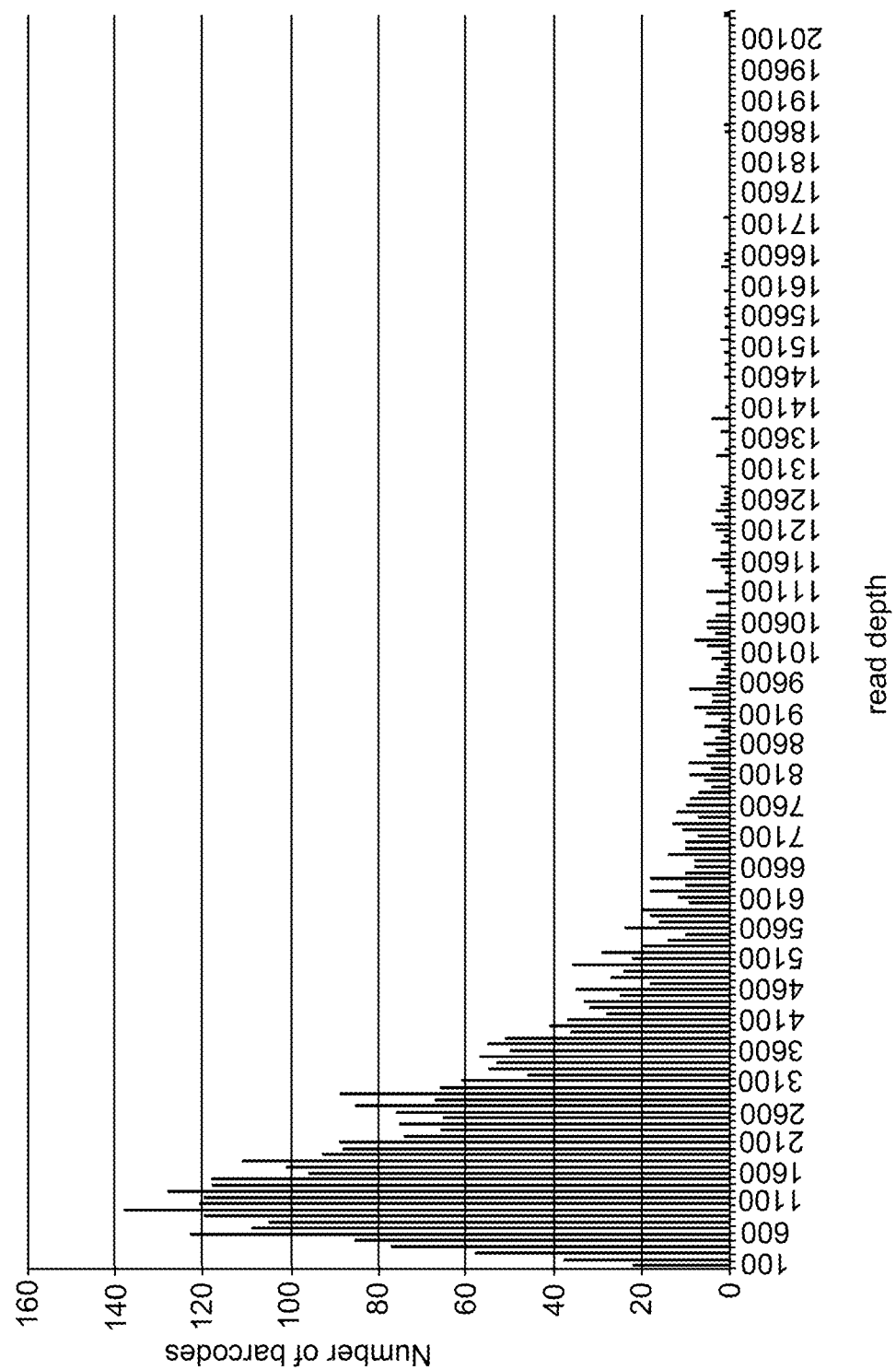
FIG. 9 is a graph showing barcode sampling frequency as studied in Example 2.

The barcode sampling frequency is in good agreement with the expected Poisson distribution (see, FIG. 9).

The sequencing error rate at each trimer level was studied. Significant sequencing errors in individual trimers in the barcode regions were observed because the sequences were different from the original 8 trimers used in constructing the barcodes. Most errors appeared to be one base error in the trimer block. Two-base errors in the trimer block were at significantly lower levels. Some errors can be corrected based on the defined relationship to one of 8 trimers used in synthesis. For example, an observed "TGA" trimer in sequencing reads most likely derived from the original "TGC" used in synthesis, so the "TGA" can be corrected to "TGC" and the barcode containing this error can be rescued.

The following table summarized the error rates at the individual trimer level. Using longer building blocks, for example 4-mers, can further enhance the power of error correction.

| | |
|---|---|
| Total occurrence of trimers | 49407609 |
| Total occurrence of correct trimers | 48332932 |
| Total occurrence of wrong trimers | 1074677 |
| Total wrong trimers that can be corrected | 299455 |
| Total wrong trimers with two errors | 115682 |

The error rate at the barcode (formed by 4 trimers) region level, i.e., how many of the barcodes are completely error free, was also estimated. Around 10% of the paired-end reads had errors in the barcode region.

Example 3

Using Semi-Random Barcode Adapter in RNA Quantification

The ERCC RNA control was used as reference materials. It contained a mixture of 92 in vitro transcribed RNA molecules at defined concentrations spanning 6 logs. Each RNA transcript had a polyA tail and ranged from 200 nucleotides to 2500 nucleotides long.

The ERCC RNA control was developed by the National Institute of Standards and Technology (NIST) and purchased from Life Technologies.

To evaluate the accuracy of RNA-seq quantification using molecular barcodes, a cDNA library of 30 ng ERCC RNA controls was constructed using semi-random Illumina adapters and NEB low input mRNA-seq protocol. The library was prepared using NEBNext Ultra Directional RNA Library Prep Kit for Illumina. 30 ng ERCC RNA Spike-In Control Mix 1 was used. The kit instructions were followed to construct the RNASeq library except semi-random barcode adapters were used instead of NEB adapters in the ligation step. After library quantification and quality control, it was sequenced on MiSeq.

Figure 10:
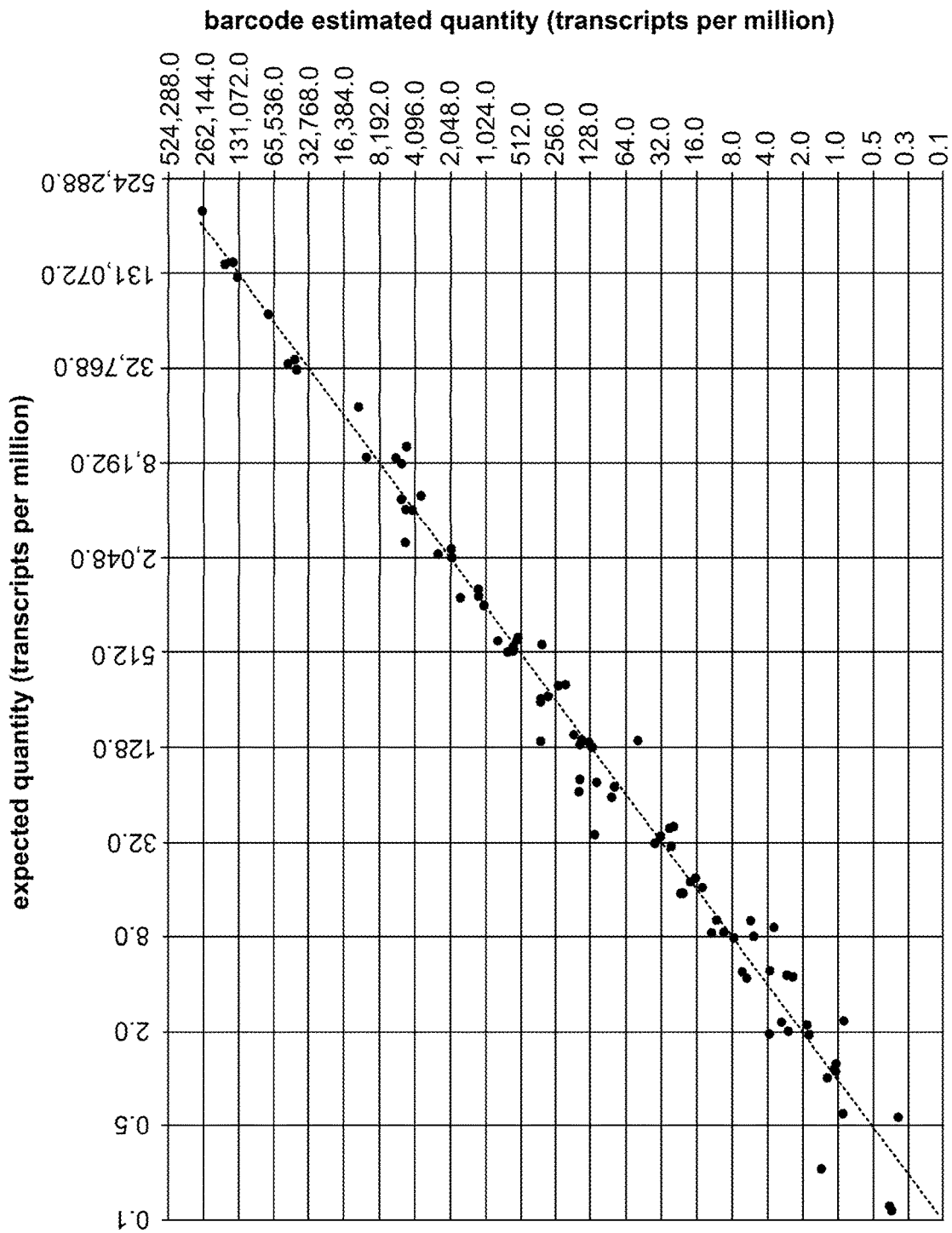
FIG. 10 is a graph showing the correlation between expected quantity and barcode count at the transcript level as studied in Example 3.

The Correlation Between Expected Quantity and Barcode Count at the Transcript Level In this analysis, the correlation between barcode counts vs. expected RNA copies was examined. The barcode counts were normalized to sequencing depth and transcript length before comparing to the expected quantity. The PEARSON correlation is 0.99 (see, FIG. 10).

The Correlation Between Read Count and Barcode Count at the Base Level

Figure 11:
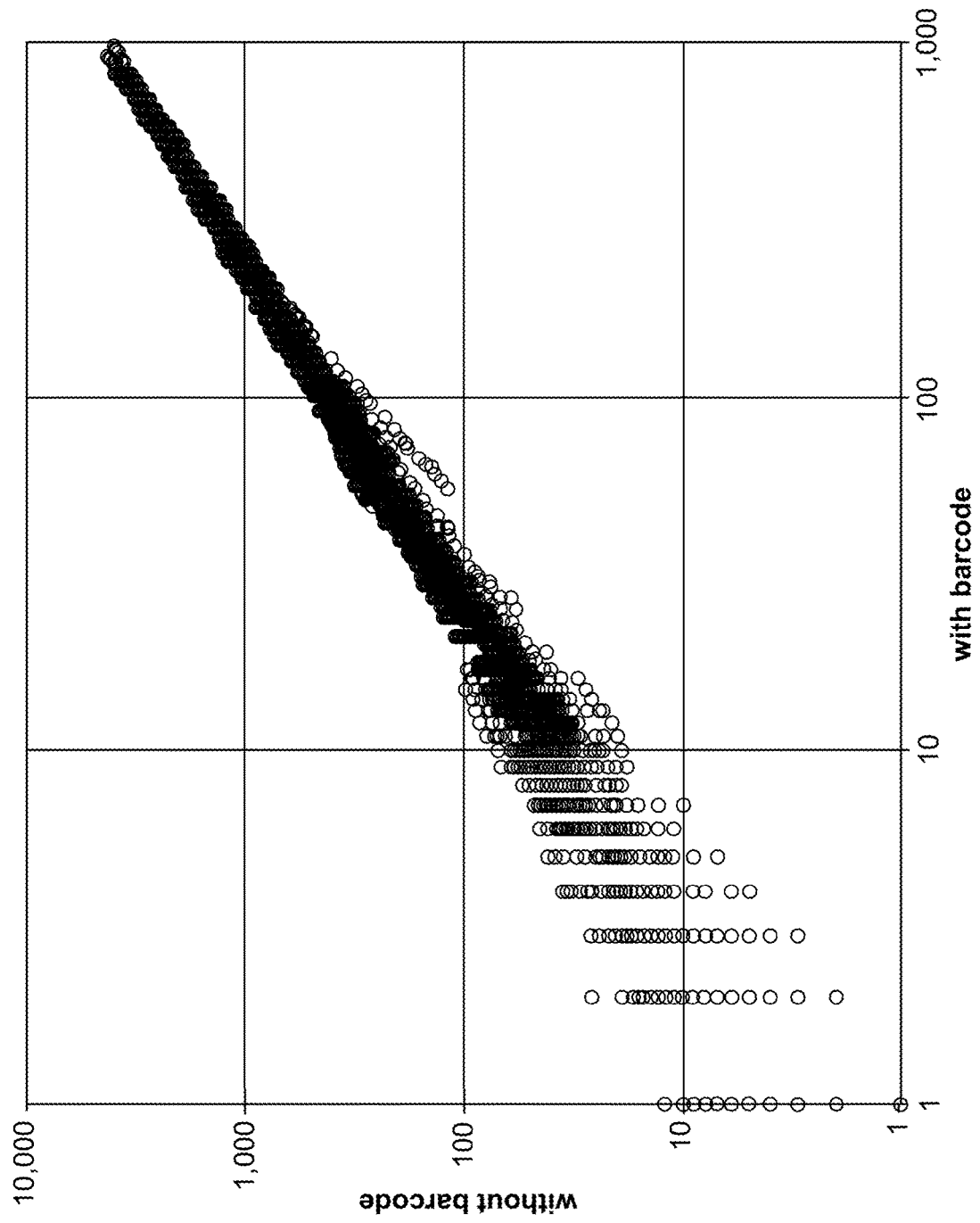
FIG. 11 is a graph showing the correlation between read count and barcode count at the base level as studied in Example 3.

The correlation between read count and barcode count at the base level is shown in FIG. 11. The scattering at the lower left corner indicates a range of PCR amplification bias for low abundant bases, where a specific barcode count corresponds to a wider range of read count. This suggests that barcode improved quantification of low abundant targets.

The Coverage Uniformity Along the Transcript

Figure 12:
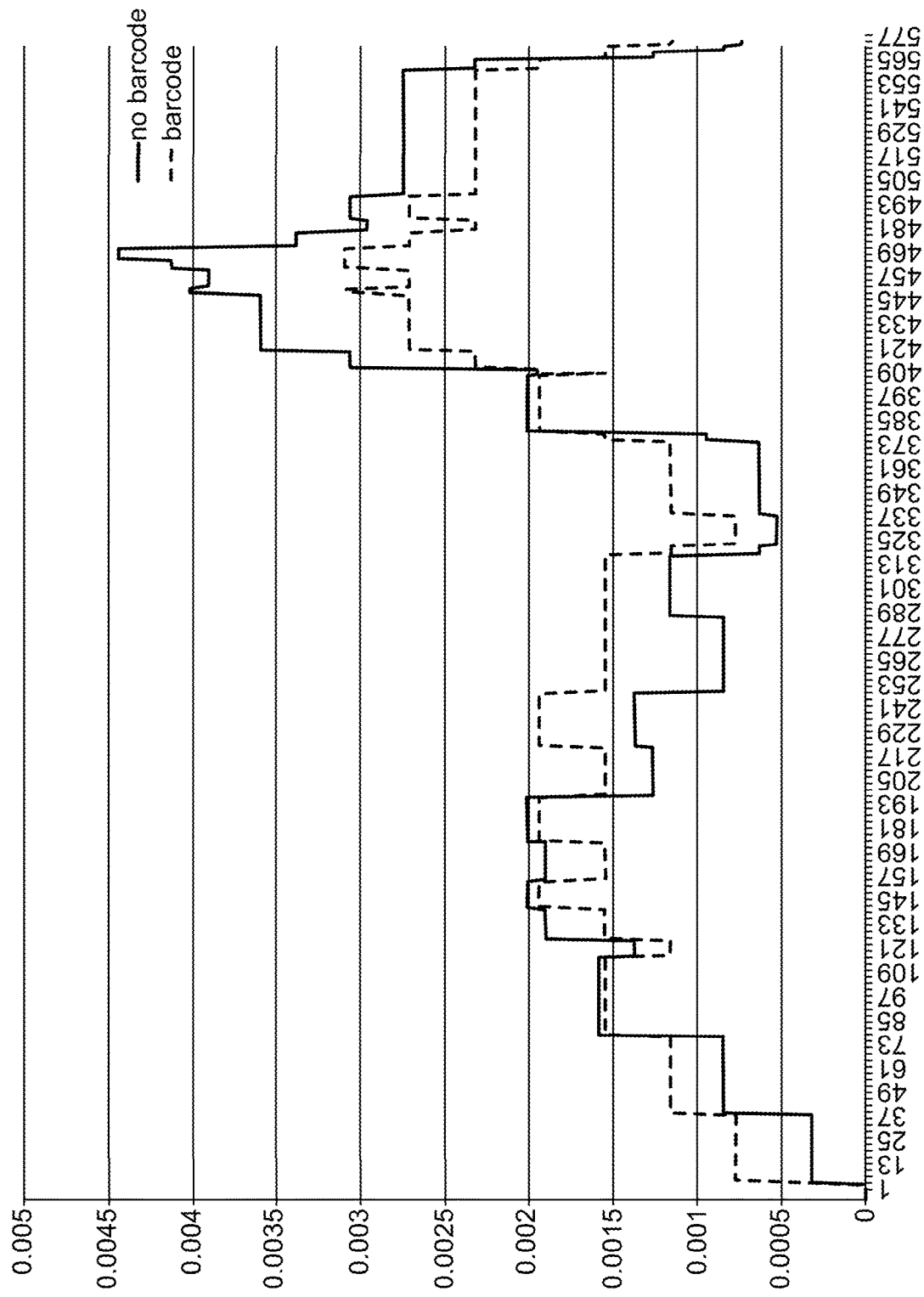
FIG. 12 is a graph showing coverage uniformity along a transcript as studied in Example 3.

The barcode count and read count for each base along a transcript were calculated. FIG. 12 illustrates one transcript, Transcript No. 73, where the coverage uniformity was better using barcode count.

Figure 13:
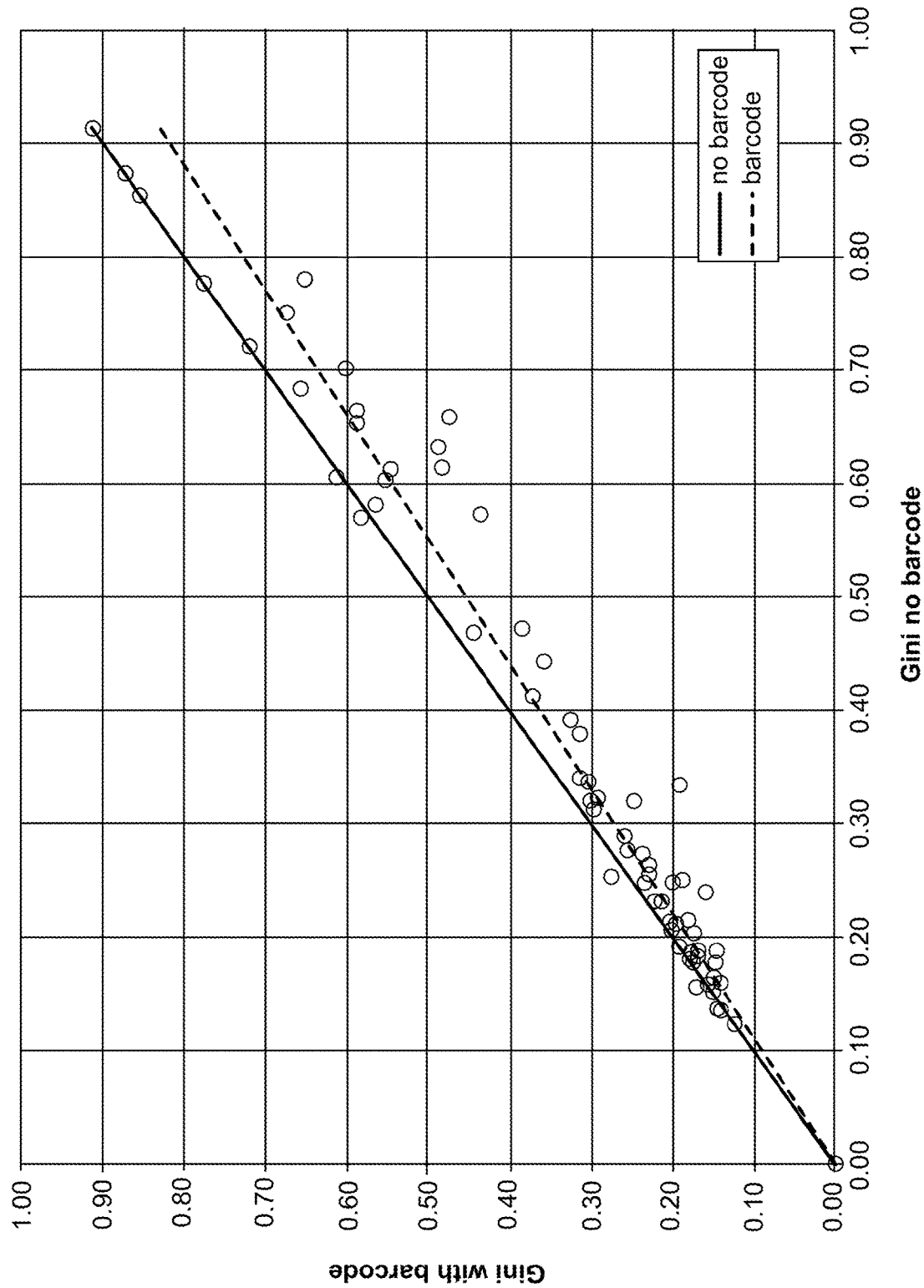
FIG. 13 is a graph showing the correlation of Gini Scores calculated with and without barcodes as studied in Example 3.

To quantify this effect, the Gini Score was used to measure uniformity along each transcript and plot the Gini scores calculated with and without barcodes. When there was a large Gini score from read count, a downward shift of Gini score was observed from barcode count (see, FIG. 13), indicating that barcode count improved coverage uniformity by removing PCR amplification bias.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A plurality of single-stranded (ss) oligonucleotides for synthesizing a sequencing library, consisting of single-stranded (ss) oligonucleotides each of which comprises from the 5' to 3' direction a 1st sequence region and a 2nd sequence region:
   (a) the $1^{st}$ sequence region is a barcode sequence consisting of (Xmer)n, wherein the Xmer is a 3-mer, 4-mer, 5-mer, or 6-mer, n is an integer from 2 to 8, and different Xmers in the $1^{st}$ sequence regions of the plurality of ss oligonucleotides have 2 or more nucleotide differences from each other, and
   (b) the $2^{nd}$ sequence region is
      (i) at least 10 nucleotides in length,
      (ii) fully or substantially complementary to a target sequence, and
      (iii) the same among the plurality of oligonucleotides,
   wherein the plurality of ss oligonucleotides comprises at least 100 different $1^{st}$ sequence regions.

2. The plurality of oligonucleotides of claim 1, wherein the Xmer is a 3-mer, and n is 3, 4, 5, 6, or 7.

3. The plurality of oligonucleotides of claim 1, wherein the total number of different Xmers in the mixture is at least 5.

4. The plurality of oligonucleotides of claim 1, wherein the Xmer is a 3-mer, and the total number of different Xmers in the mixture is at least 8.

5. The plurality of oligonucleotides of claim 1, wherein each ss oligonucleotide further comprises
   (c) a $3^{rd}$ sequence region that
      (i) has a defined sequence that is 3 to 8 nucleotides in length,
      (ii) is located 5' to the $2^{nd}$ sequence region, and
      (iii) is the same among the oligonucleotides.

6. The plurality of oligonucleotides of claim 5, wherein the $3^{rd}$ sequence region is located 5' to the $1^{st}$ sequence region.

7. The plurality of oligonucleotides of claim 5, wherein each of the ss oligonucleotides further comprises
   (d) a $4^{th}$ sequence region that is
      (i) located 3' to the $2^{nd}$ sequence region, and
      (ii) the same among the oligonucleotides.

8. The plurality of oligonucleotides of claim 1, wherein the 5' terminus of the ss oligonucleotide is phosphorylated.

9. The plurality of oligonucleotides of claim 1, wherein the target sequence is a portion at least 10 nucleotides long of one strand of an at least partially double-stranded sequencing adaptor.

10. A plurality of single-stranded (ss) oligonucleotides for synthesizing a sequencing library, consisting of single-stranded (ss) oligonucleotides each of which comprises from the 5' to 3' direction a $1^{st}$ sequence region and a $2^{nd}$ sequence region:
    (a) the $1^{st}$ sequence region is a barcode sequence consisting of (Xmer)n, wherein the Xmer is a 4-mer or 5-mer, n is an integer from 2 to 8, and the total number of different Xmers in the $1^{st}$ sequence regions of the plurality of ss oligonucleotides is 2 to 25, and
    (b) the $2^{nd}$ sequence region is
       (i) at least 10 nucleotides in length,
       (ii) fully or substantially complementary to a target sequence, and
       (iii) the same among the plurality of ss oligonucleotides,
    wherein the plurality of ss oligonucleotides comprises at least 100 different $1^{st}$ sequence regions.

11. The plurality of oligonucleotides of claim 10, wherein the Xmer is a 4-mer, and n is 2, 3, 4, 5, 6, or 7.

12. The plurality of oligonucleotides of claim 10, wherein the total number of different Xmers in the mixture is at least 5.

13. The plurality of oligonucleotides of claim 10, wherein the Xmer is a 4-mer, and the total number of different Xmers in the mixture is at least 8.

14. The plurality of oligonucleotides of claim 10, wherein each oligonucleotide further comprises
    (c) a $3^{rd}$ sequence region that
       (iv) has a defined sequence that is 3 to 8 nucleotides in length,
       (v) is located 5' to the $2^{nd}$ sequence region, and
       (vi) is the same among the oligonucleotides.

15. The plurality of oligonucleotides of claim 14, wherein the $3^{rd}$ sequence region is located 5' to the $1^{st}$ sequence region.

16. The plurality of oligonucleotides of claim 14, wherein each of the ss oligonucleotides further comprises
    (d) a $4^{th}$ sequence region that is
       (iii) located 3' to the $2^{nd}$ sequence region, and
       (iv) the same among the oligonucleotides.

17. The plurality of oligonucleotides of claim 10, wherein the 5' terminus of the ss oligonucleotide is phosphorylated.

18. The plurality of oligonucleotides of claim 10, wherein the target sequence is a portion at least 10 nucleotides long of one strand of an at least partially double-stranded sequencing adaptor.

19. The plurality of oligonucleotides of claim 1, wherein the $2^{nd}$ sequence region does not comprise poly(T).

20. The plurality of oligonucleotides of claim 19, wherein the $2^{nd}$ sequence region does not comprise 6 to 20 thymidines.

21. The plurality of oligonucleotides of claim 10, wherein the $2^{nd}$ sequence region does not comprise poly(T).

22. The plurality of oligonucleotides of claim 21, wherein the $2^{nd}$ sequence region does not comprise 6 to 20 thymidines.

* * * * *

UNITED STATES PATENT AND TRADEMARK OFFICE
CERTIFICATE OF CORRECTION

PATENT NO. : 12,398,391 B2  
APPLICATION NO. : 14/796279  
DATED : August 26, 2025  
INVENTOR(S) : Yexun Wang et al.

It is certified that error appears in the above-identified patent and that said Letters Patent is hereby corrected as shown below:

In the Claims

In Column 43, Line 2, cancel the text beginning with "1. A plurality of a single-stranded (ss)" to and ending with "6 to 20 thymidines." in Column 44, Line 52.
Please insert the following claims:
-- 1. A plurality of single-stranded (ss) oligonucleotides for synthesizing a sequencing library, consisting of single-stranded (ss) oligonucleotides each of which comprises from the 5' to 3' direction a 1st sequence region and a 2nd sequence region:

(a) the $1^{st}$ sequence region is a barcode sequence consisting of (Xmer)n, wherein the Xmer is a 3-mer, 4-mer, 5-mer, or 6-mer, n is an integer from 2 to 8, and different Xmers in the $1^{st}$ sequence regions of the plurality of ss oligonucleotides have 2 or more nucleotide differences from each other, and (b) the $2^{nd}$ sequence region is
        (i) at least 10 nucleotides in length,
        (ii) fully or substantially complementary to a target sequence, and
        (iii) the same among the plurality of oligonucleotides, wherein the plurality of ss oligonucleotides comprises at least 100 different $1^{st}$ sequence regions.

2. The plurality of oligonucleotides of claim 1, wherein the Xmer is a 3-mer, and n is 3, 4, 5, 6, or 7.

3. The plurality of oligonucleotides of claim 1, wherein the Xmer is a 4-mer, and n is 3, 4, 5, or 6.

4. The plurality of oligonucleotides of claim 1, wherein the total number of different Xmers in the mixture is at least 5.

5. The plurality of oligonucleotides of claim 1, wherein the Xmer is a 3-mer, and the total number of different Xmers in the mixture is at least 8.

Signed and Sealed this  
Eighteenth Day of November, 2025

John A. Squires  
*Director of the United States Patent and Trademark Office*

6. The plurality of oligonucleotides of claim 1, wherein each ss oligonucleotide further comprises
    (c) a 3$^{rd}$ sequence region that
        (i) has a defined sequence that is 3 to 8 nucleotides in length,
        (ii) is located 5' to the 2$^{nd}$ sequence region, and
        (iii) is the same among the oligonucleotides.

7. The plurality of oligonucleotides of claim 6, wherein the 3$^{rd}$ sequence region is located 5' to the 1$^{st}$ sequence region.

8. The plurality of oligonucleotides of claim 6, wherein each of the ss oligonucleotides further comprises
    (d) a 4$^{th}$ sequence region that is
        (i) located 3' to the 2$^{nd}$ sequence region, and
        (ii) the same among the oligonucleotides.

9. The plurality of oligonucleotides of claim 1, wherein the 5' terminus of the ss oligonucleotide is phosphorylated.

10. The plurality of oligonucleotides of claim 1, wherein the target sequence is a portion at least 10 nucleotides long of one strand of an at least partially double-stranded sequencing adaptor.

11. The plurality of oligonucleotides of claim 1, wherein each ss oligonucleotide is a reverse transcription primer, and wherein the 2$^{nd}$ sequence region comprises poly(T).

12. The plurality of oligonucleotides of claim 11, wherein each of the ss oligonucleotides further comprises:
    (d) a 4$^{th}$ sequence region that is
        (i) located 5' to the 1$^{st}$ sequence region, the 2$^{nd}$ sequence region, and the 3$^{rd}$ sequence region if present, and
        (ii) the same among the oligonucleotides.

13. The plurality of oligonucleotides of claim 1, wherein each oligonucleotide is a PCR primer, and wherein the target sequence comprises a conserved sequence of a region of interest.

14. The plurality of oligonucleotides of claim 13, wherein each of the ss oligonucleotides further comprises:
    (d) a 4$^{th}$ sequence region that is
        (i) located 5' to the 1$^{st}$ sequence region, the 2$^{nd}$ sequence region, and the 3$^{rd}$ sequence region if present, and
        (ii) the same among the oligonucleotides.

15. The plurality of oligonucleotides of claim 13, wherein the region of interest is a 16S RNA gene.

16. A plurality of sets of single-stranded (ss) oligonucleotides, wherein each set comprises the plurality of ss oligonucleotides of claim 6, and wherein the oligonucleotides in different sets are identical to each other except in the $3^{rd}$ sequence regions thereof.

17. A kit for preparing a plurality of double-stranded (ds) sequencing adapters, comprising:
    (i) (a) the plurality of ss oligonucleotides of claim 1, or
    (b) the plurality of sets of oligonucleotides, wherein each set comprises a plurality of ss oligonucleotides, wherein each oligonucleotide comprises the $1^{st}$ sequence region and the $2^{nd}$ sequence region of claim 1, and further comprises a $3^{rd}$ sequence region that (1) has a defined sequence that is 3 to 8 nucleotides in length, (2) is located 5' to the $2^{nd}$ sequence region, and (3) is the same among the oligonucleotides, and wherein the oligonucleotides in different sets are identical to each other except in the $3^{rd}$ sequence regions thereof, and
    (ii) a 2nd ss oligonucleotide that comprises the target sequence ("Sequence B").

18. A plurality of double-stranded (ds) sequencing adapters, wherein each sequencing adapter comprises:
    (a) an oligonucleotide ("$1^{st}$ oligonucleotide") of the plurality of single-stranded (ss) oligonucleotides of claim 1, and
    (b) a $2^{nd}$ ss oligonucleotide that comprises from the 3' to 5' direction
    (i) a sequence ("Sequence A") that is fully complementary to the $1^{st}$ sequence region of the $1^{st}$ oligonucleotide of the sequencing adapter, and
    (ii) the target sequence ("Sequence B"), and
wherein the $1^{st}$ oligonucleotide anneals to the $2^{nd}$ ss oligonucleotide.

19. The plurality of ds sequencing adapters of claim 18, wherein the $1^{st}$ oligonucleotide comprises the $3^{rd}$ sequence region, and wherein the 2nd oligonucleotide further comprises
    (iii) a sequence ("Sequence C") that is located 3' to Sequence B, and is fully complementary to the $3^{rd}$ sequence region of the $1^{st}$ oligonucleotide.

20. The plurality of ds sequencing adapters of claim 18, wherein the $2^{nd}$ oligonucleotide further comprises
    (iv) a sequence ("Sequence D") located 5' to Sequence B.

21. The plurality of ds sequencing adapters of claim 20, wherein Sequence D of the $2^{nd}$ oligonucleotide is not complementary to the $4^{th}$ sequence region, if present, of the $1^{st}$ oligonucleotide.

22. The plurality of ds sequencing adapters of claim 18, wherein each ds sequencing adapter has a single nucleotide 3'-overhang in the $2^{nd}$ oligonucleotide.

23. A plurality of sets of double-stranded (ds) sequencing adapters, wherein
    (A) each set comprises a plurality of single-stranded (ss) sequencing adapters, wherein each sequencing adapter in each set comprises:

(a) an oligonucleotide ("1st oligonucleotide") of the plurality of ss oligonucleotides of claim 6, and (b) a 2nd ss oligonucleotide that comprises:

(i) a sequence ("Sequence A") that is fully complementary to the 1st sequence region of the 1st oligonucleotide of the sequence adapter, and (ii) the target sequence ("Sequence B") located 5' to Sequence A, and (iii) a sequence ("Sequence C") that is located 3' to Sequence B and is fully complementary to the 3rd sequence region of the 1st oligonucleotide, and wherein the 1st oligonucleotide anneals to the 2nd oligonucleotide; and (B) wherein the plurality of ds sequencing adapters in different sets are identical to each other except in the 3rd sequence region of the 1st oligonucleotide and in Sequence C of the 2nd oligonucleotide.

24. A kit for preparing a sequencing library, comprising:
    (i) the plurality of double-stranded (ds) sequencing adapters of claim 18, and
    (ii) a DNA ligase.

25. A method for preparing a plurality of sequencing libraries, comprising:
    (1) ligating the sequencing adapters of each set of the plurality of sets of double-stranded (ds) sequencing adapters of claim 23 to ds DNA fragments of each of a plurality of samples, thereby generating a plurality of sequencing libraries.

26. A method for preparing a sequencing library, comprising:
    (1) (a) reverse transcribing mRNAs of a sample in the presence of the plurality of single stranded (ss) oligonucleotides of claim 1 to generate cDNAs, wherein each oligonucleotide is a reverse transcription primer, and wherein the 2nd sequence region comprises poly(T), or
    (b) amplifying a region of interest in a sample in the presence of the plurality of ss oligonucleotides of claim 1 to generate amplified DNAs, wherein each oligonucleotide is a PCR primer, and wherein the target sequence comprises a conserved sequence of a region of interest, and
    (2) attaching the cDNAs or amplified DNA of step (1) to at least one double-stranded (ds) sequencing adapter, thereby generating a sequencing library.

27. A method for preparing a sequencing library, comprising:
    (1) reverse transcribing mRNAs of a sample in the presence of the plurality of ss oligonucleotides of claim 12 to generate cDNAs, and
    (2) amplifying cDNAs
        (a) in the presence of a primer that comprises the 4th sequence region, wherein the 4th sequence region comprises a sequencing adapter sequence, and wherein the primer is preferably not any of the plurality of ss oligonucleotides, or
        (b) in the presence of a primer comprising, from the 3' to 5' direction, the 4th sequence region and a sequencing adapter sequence, wherein the 4th sequence region does not comprise a sequencing adapter sequence, thereby generating a sequencing library.

28. A method for preparing a sequencing library, comprising:
(a) amplifying nucleic acids of a region of interest in a sample in the presence of the plurality of ss oligonucleotides of claim 14 wherein the 4$^{th}$ sequence region comprises a sequencing adapter sequence, thereby generating a sequence library; or
(b) (1) amplifying nucleic acids of a region of interest in a sample in the presence of the plurality of ss oligonucleotides of claim 14 wherein the 4$^{th}$ sequence region does not comprises a sequencing adapter sequence to generate amplified nucleic acids, and
(2) further amplifying the amplified nucleic acids of step (b)(1) in the presence of a primer that comprises from the 5' to 3' direction, the 4$^{th}$ sequence and a sequencing adapter sequence, thereby generating a sequencing library.

29. A kit for preparing a sequencing library, comprising:
(1) the plurality of single-stranded (ss) oligonucleotides of claim 12, and
(2) a DNA polymerase.

30. A kit for preparing a sequencing library, comprising:
(i) the plurality of sets of double-stranded (ds) sequencing adapters of claim 23, and
(ii) a DNA ligase.

31. A kit for preparing a sequencing library, comprising:
(1) the plurality of single-stranded (ss) oligonucleotides of claim 14, and
(2) a DNA polymerase.

32. A plurality of single-stranded (ss) oligonucleotides for synthesizing a sequencing library, consisting of single-stranded (ss) oligonucleotides each of which comprises from the 5' to 3' direction a 1$^{st}$ sequence region and a 2$^{nd}$ sequence region:
(a) the 1$^{st}$ sequence region is a barcode sequence consisting of (Xmer)n, wherein the Xmer is a 4-mer or 5-mer, n is an integer from 2 to 8, and the total number of different Xmers in the 1$^{st}$ sequence regions of the plurality of ss oligonucleotides is 2 to 25, and
(b) the 2$^{nd}$ sequence region is
(i) at least 10 nucleotides in length,
(ii) fully or substantially complementary to a target sequence, and
(iii) the same among the plurality of ss oligonucleotides,
wherein the plurality of ss oligonucleotides comprises at least 100 different 1$^{st}$ sequence regions.

33. The plurality of oligonucleotides of claim 32, wherein the Xmer is a 4-mer, and n is 2, 3, 4, 5, 6, or 7.

34. The plurality of oligonucleotides of claim 32, wherein the total number of different Xmers in the mixture is at least 5.

35. The plurality of oligonucleotides of claim 32, wherein the Xmer is a 4-mer, and the total number of different Xmers in the mixture is at least 8.

36. The plurality of oligonucleotides of claim 32, wherein each oligonucleotide further comprises
 (c) a 3$^{rd}$ sequence region that
  (iv) has a defined sequence that is 3 to 8 nucleotides in length,
  (v) is located 5' to the 2$^{nd}$ sequence region, and
  (vi) is the same among the oligonucleotides.

37. The plurality of oligonucleotides of claim 36, wherein the 3$^{rd}$ sequence region is located 5' to the 1$^{st}$ sequence region.

38. The plurality of oligonucleotides of claim 36, wherein each of the ss oligonucleotides further comprises
 (d) a 4$^{th}$ sequence region that is
  (iii) located 3' to the 2$^{nd}$ sequence region, and
  (iv) the same among the oligonucleotides.

39. The plurality of oligonucleotides of claim 32, wherein the 5' terminus of the ss oligonucleotide is phosphorylated.

40. The plurality of oligonucleotides of claim 32, wherein the target sequence is a portion at least 10 nucleotides long of one strand of an at least partially double-stranded sequencing adaptor.

41. The plurality of oligonucleotides of claim 1, wherein the 2$^{nd}$ sequence region does not comprise poly(T).

42. The plurality of oligonucleotides of claim 41, wherein the 2$^{nd}$ sequence region does not comprise 6 to 20 thymidines.

43. The plurality of oligonucleotides of claim 32, wherein the 2$^{nd}$ sequence region does not comprise poly(T).

44. The plurality of oligonucleotides of claim 43, wherein the 2$^{nd}$ sequence region does not comprise 6 to 20 thymidines. --.